(12) United States Patent
Snead et al.

(10) Patent No.: US 9,000,246 B2
(45) Date of Patent: Apr. 7, 2015

(54) METHODS OF REFINING AND PRODUCING DIBASIC ESTERS AND ACIDS FROM NATURAL OIL FEEDSTOCKS

(71) Applicants: Thomas E. Snead, Bolingbrook, IL (US); Steven A. Cohen, Naperville, IL (US); Demond L. Gildon, Romeoville, IL (US)

(72) Inventors: Thomas E. Snead, Bolingbrook, IL (US); Steven A. Cohen, Naperville, IL (US); Demond L. Gildon, Romeoville, IL (US)

(73) Assignee: Elevance Renewable Sciences, Inc., Woodridge, IL (US)

(*) Notice: Subject to any disclaimer, the term of this patent is extended or adjusted under 35 U.S.C. 154(b) by 409 days.

(21) Appl. No.: 13/647,809

(22) Filed: Oct. 9, 2012

(65) Prior Publication Data

US 2013/0085288 A1  Apr. 4, 2013

Related U.S. Application Data

(63) Continuation-in-part of application No. 12/901,829, filed on Oct. 11, 2010.

(60) Provisional application No. 61/250,743, filed on Oct. 12, 2009.

(51) Int. Cl.
  *C07C 1/00* (2006.01)
  *C07C 5/03* (2006.01)
  (Continued)

(52) U.S. Cl.
  CPC . *C11C 3/00* (2013.01); *C10G 45/00* (2013.01); *C10G 45/58* (2013.01); *C10G 50/00* (2013.01); *C10G 65/043* (2013.01); *C11B 3/00* (2013.01);

*C10L 1/026* (2013.01); *C10L 1/08* (2013.01); *C11C 3/003* (2013.01); *C10G 3/42* (2013.01); *C10G 2300/30* (2013.01); *C10G 2300/301* (2013.01); *C10G 2300/307* (2013.01);
(Continued)

(58) Field of Classification Search
  USPC ............ 554/170; 585/14, 240, 250, 310, 324, 585/638, 639, 640
  See application file for complete search history.

(56) References Cited

U.S. PATENT DOCUMENTS 2,484,841 A   10/1949  Lorand
3,150,205 A    9/1964  Krane et al.
(Continued)

FOREIGN PATENT DOCUMENTS

EP        0167201 B2    11/1995
EP        0168091 B2     4/2003
(Continued)

OTHER PUBLICATIONS

Schrock, "High Oxidation State Multiple Metal-Carbon Bonds" Chem. Rev., 102, 2002, pp. 145-179.
(Continued)

*Primary Examiner* — Thuan D Dang
(74) *Attorney, Agent, or Firm* — Robert S. Dailey

(57) ABSTRACT

Methods are provided for refining natural oil feedstocks and producing dibasic esters and/or dibasic acids. The methods comprise reacting a terminal olefin with an internal olefin in the presence of a metathesis catalyst to form a dibasic ester and/or dibasic acid. In certain embodiments, the olefin esters are formed by reacting the feedstock in the presence of a metathesis catalyst under conditions sufficient to form a metathesized product comprising olefins and esters, separating the olefins from the esters in the metathesized product, and transesterifying the esters in the presence of an alcohol to form a transesterified product having olefin esters.

21 Claims, 2 Drawing Sheets

(51) Int. Cl.

| | | |
|---|---|---|
| C07C 1/24 | (2006.01) | |
| C11C 3/00 | (2006.01) | |
| C10G 45/00 | (2006.01) | |
| C10G 45/58 | (2006.01) | |
| C10G 50/00 | (2006.01) | |
| C10G 65/04 | (2006.01) | |
| C11B 3/00 | (2006.01) | |
| C10L 1/02 | (2006.01) | |
| C10L 1/08 | (2006.01) | |
| C10G 3/00 | (2006.01) | |
| C07C 67/03 | (2006.01) | |
| C07C 67/333 | (2006.01) | |
| C07C 67/475 | (2006.01) | |

(52) U.S. Cl.
CPC ...... C10G2300/308 (2013.01); C10G 2300/44 (2013.01); C10G 2400/02 (2013.01); C10G 2400/04 (2013.01); C10G 2400/08 (2013.01); C10G 2400/20 (2013.01); C10G 2400/22 (2013.01); C10G 2300/1014 (2013.01); C10G 2300/1018 (2013.01); C10G 2300/1088 (2013.01); *C07C 67/03* (2013.01); *C07C 67/333* (2013.01); *C07C 67/475* (2013.01); C10L 2200/0469 (2013.01); C10L 2200/0476 (2013.01)

(56) References Cited

U.S. PATENT DOCUMENTS

| | | |
|---|---|---|
| 3,351,566 A | 11/1967 | Taylor et al. |
| 3,507,890 A | 4/1970 | Dieckmann et al. |
| 4,210,771 A | 7/1980 | Holcombe |
| 4,465,890 A | 8/1984 | Kukes et al. |
| 4,554,065 A | 11/1985 | Albinson et al. |
| 4,943,396 A | 7/1990 | Johnson |
| 4,992,605 A | 2/1991 | Craig et al. |
| 5,043,485 A | 8/1991 | Fleckenstein et al. |
| 5,091,116 A | 2/1992 | Krishnamurthy et al. |
| 5,095,169 A | 3/1992 | Skeels et al. |
| 5,113,030 A | 5/1992 | Chen et al. |
| 5,120,896 A | 6/1992 | Kemp et al. |
| 5,146,033 A | 9/1992 | Schrock et al. |
| 5,191,145 A | 3/1993 | Allen et al. |
| 5,262,076 A | 11/1993 | Ishida et al. |
| 5,264,606 A | 11/1993 | Moloy et al. |
| 5,298,271 A | 3/1994 | Takashina et al. |
| 5,342,909 A | 8/1994 | Grubbs et al. |
| 5,348,755 A | 9/1994 | Roy |
| 5,374,751 A | 12/1994 | Cheng et al. |
| 5,391,385 A | 2/1995 | Seybold |
| 5,399,731 A | 3/1995 | Wimmer |
| 5,401,866 A | 3/1995 | Cheng et al. |
| 5,414,184 A | 5/1995 | Wu et al. |
| 5,432,083 A | 7/1995 | Copeland et al. |
| 5,484,201 A | 1/1996 | Goolsbee |
| 5,532,163 A | 7/1996 | Yagi et al. |
| 5,560,950 A | 10/1996 | Conte et al. |
| 5,596,111 A | 1/1997 | Sibi et al. |
| 5,597,600 A | 1/1997 | Munson et al. |
| 5,653,966 A | 8/1997 | Bertoli et al. |
| 5,672,802 A | 9/1997 | Lutz |
| 5,675,051 A | 10/1997 | Chauvin et al. |
| 5,747,409 A | 5/1998 | Commereuc |
| 5,824,354 A | 10/1998 | Ritter et al. |
| 5,840,942 A | 11/1998 | Oude Alink |
| 5,864,049 A | 1/1999 | Dos Santos et al. |
| 5,880,298 A | 3/1999 | Hillion et al. |
| 5,883,272 A | 3/1999 | Noweck et al. |
| 5,932,261 A | 8/1999 | Unnithan |
| 5,939,572 A | 8/1999 | Sibi et al. |
| 5,959,129 A | 9/1999 | van Dam et al. |
| 5,972,057 A | 10/1999 | Hayafuji et al. |
| 6,033,706 A | 3/2000 | Silkeberg et al. |
| 6,075,158 A | 6/2000 | Hill |
| 6,127,560 A | 10/2000 | Stidham et al. |
| 6,127,561 A | 10/2000 | Jeromin et al. |
| 6,129,945 A | 10/2000 | Awad et al. |
| 6,162,480 A | 12/2000 | van Buuren et al. |
| 6,172,248 B1 | 1/2001 | Copeland et al. |
| 6,175,047 B1 | 1/2001 | Hori et al. |
| 6,207,209 B1 | 3/2001 | Jirjis et al. |
| 6,210,732 B1 | 4/2001 | Papanton |
| 6,214,764 B1 | 4/2001 | Gillespie |
| 6,215,019 B1 | 4/2001 | Pederson et al. |
| 6,248,911 B1 | 6/2001 | Canessa et al. |
| 6,251,460 B1 | 6/2001 | Ganguli et al. |
| 6,265,495 B1 | 7/2001 | Hirata et al. |
| 6,271,430 B2 | 8/2001 | Schwab et al. |
| 6,284,852 B1 | 9/2001 | Lynn et al. |
| 6,288,251 B1 | 9/2001 | Tsuto et al. |
| 6,303,837 B1 | 10/2001 | Gürtler et al. |
| 6,313,365 B1 | 11/2001 | Hori et al. |
| 6,368,648 B1 | 4/2002 | Bertram et al. |
| 6,376,581 B1 | 4/2002 | Tanaka et al. |
| 6,388,038 B1 | 5/2002 | Hirata et al. |
| 6,395,669 B1 | 5/2002 | Sartain et al. |
| 6,409,778 B1 | 6/2002 | Auschra et al. |
| 6,440,057 B1 | 8/2002 | Ergün et al. |
| 6,492,564 B1 | 12/2002 | Wiese et al. |
| 6,506,944 B1 | 1/2003 | Schwab et al. |
| 6,552,139 B1 | 4/2003 | Herrmann et al. |
| 6,552,208 B1 | 4/2003 | Alander et al. |
| 6,583,236 B1 | 6/2003 | Giardello et al. |
| 6,605,748 B2 | 8/2003 | Wagener et al. |
| 6,638,551 B1 | 10/2003 | Levy et al. |
| 6,646,172 B1 | 11/2003 | Schwab et al. |
| 6,677,495 B1 | 1/2004 | Schwab et al. |
| 6,696,597 B2 | 2/2004 | Pedersen et al. |
| 6,706,299 B2 | 3/2004 | Thengumpillil et al. |
| 6,740,134 B2 | 5/2004 | Angelico et al. |
| 6,761,869 B1 | 7/2004 | Virtanen |
| 6,800,316 B1 | 10/2004 | Perrut et al. |
| 6,833,149 B2 | 12/2004 | Jirjis et al. |
| 6,846,772 B2 | 1/2005 | Lok et al. |
| 6,852,900 B2 | 2/2005 | Wurziger et al. |
| 6,900,347 B2 | 5/2005 | Paulson et al. |
| 6,916,448 B2 | 7/2005 | Commereuc et al. |
| 6,960,272 B1 | 11/2005 | Tokas et al. |
| 6,962,729 B2 | 11/2005 | Tokas et al. |
| 6,982,155 B1 | 1/2006 | Fukuda et al. |
| 6,998,050 B2 | 2/2006 | Nakajoh et al. |
| 7,025,851 B2 | 4/2006 | Caster et al. |
| 7,045,100 B2 | 5/2006 | Ergün et al. |
| 7,045,114 B2 | 5/2006 | Tonkovich et al. |
| 7,060,316 B2 | 6/2006 | Sakai et al. |
| 7,067,584 B2 | 6/2006 | Rink et al. |
| 7,119,216 B2 | 10/2006 | Newman et al. |
| 7,141,083 B2 | 11/2006 | Jordan |
| 7,144,433 B2 | 12/2006 | Jordan |
| 7,144,435 B2 | 12/2006 | Jordan |
| 7,160,338 B2 | 1/2007 | Jordan |
| 7,160,339 B2 | 1/2007 | Jordan |
| 7,176,336 B2 | 2/2007 | Maughon et al. |
| 7,220,289 B2 | 5/2007 | Jordan |
| 7,276,616 B2 | 10/2007 | Dwyer et al. |
| 7,320,809 B2 | 1/2008 | Friedman et al. |
| 7,361,621 B2 | 4/2008 | Yang et al. |
| 7,431,749 B2 | 10/2008 | Kim et al. |
| 7,442,248 B2 | 10/2008 | Timmons |
| 7,449,591 B2 | 11/2008 | Brenner et al. |
| 7,452,515 B1 | 11/2008 | Lafleur et al. |
| 7,507,846 B2 | 3/2009 | Pelly |
| 7,507,854 B2 | 3/2009 | Lee et al. |
| 7,511,101 B2 | 3/2009 | Nguyen et al. |
| 7,553,982 B1 | 6/2009 | Morris |
| 7,563,915 B2 | 7/2009 | Matson et al. |
| 7,576,227 B2 | 8/2009 | Lysenko et al. |
| 7,585,990 B2 | 9/2009 | van Toor et al. |
| 7,597,783 B2 | 10/2009 | Kruidenberg |
| 7,598,407 B2 | 10/2009 | Kruidenberg |
| 7,601,309 B2 | 10/2009 | Krupa et al. |

(56) References Cited

U.S. PATENT DOCUMENTS

| | | |
|---|---|---|
| 7,612,221 B2 | 11/2009 | Haas et al. |
| 7,626,047 B2 | 12/2009 | Nakayama et al. |
| 7,626,048 B2 | 12/2009 | Soane et al. |
| 7,645,807 B1 | 1/2010 | Goetsch et al. |
| 7,652,145 B2 | 1/2010 | Herrmann et al. |
| 7,652,156 B2 | 1/2010 | Hillion et al. |
| 7,666,234 B2 | 2/2010 | Ghosh et al. |
| 7,671,224 B2 | 3/2010 | Winde et al. |
| 7,695,533 B2 | 4/2010 | Kovacs et al. |
| 7,696,376 B2 | 4/2010 | Furuta |
| 7,696,398 B2 | 4/2010 | Burdett et al. |
| 7,718,833 B2 | 5/2010 | Potthast et al. |
| 7,737,233 B2 | 6/2010 | Obrecht et al. |
| 7,743,828 B2 | 6/2010 | Roddy et al. |
| 7,745,652 B2 | 6/2010 | Lysenko et al. |
| 7,750,172 B2 | 7/2010 | Grubbs et al. |
| 7,790,651 B2 | 9/2010 | Lin et al. |
| 7,806,945 B2 | 10/2010 | Jackam et al. |
| 7,812,185 B2 | 10/2010 | Burdett et al. |
| 7,812,187 B2 | 10/2010 | Kawashima et al. |
| 7,838,711 B2 | 11/2010 | Herweck et al. |
| 7,846,995 B2 | 12/2010 | Ong et al. |
| 7,858,710 B2 | 12/2010 | Wagener et al. |
| 7,863,471 B2 | 1/2011 | Krause et al. |
| 7,875,736 B2 | 1/2011 | Wang et al. |
| 7,902,417 B2 | 3/2011 | Goldman et al. |
| 7,905,288 B2 | 3/2011 | Kinkead |
| 7,906,665 B2 | 3/2011 | Lin et al. |
| 7,939,688 B2 | 5/2011 | Meudt et al. |
| 7,951,967 B2 | 5/2011 | Chun et al. |
| 7,960,598 B2 | 6/2011 | Spilker et al. |
| 8,039,652 B2 | 10/2011 | Portnoff et al. |
| 8,039,653 B2 | 10/2011 | Soane et al. |
| 8,044,149 B2 | 10/2011 | Iwasaki et al. |
| 8,066,954 B2 | 11/2011 | Nguyen et al. |
| 8,071,799 B2 | 12/2011 | Olson |
| 8,147,766 B2 | 4/2012 | Spilker et al. |
| 8,148,477 B2 | 4/2012 | Saita et al. |
| 8,163,946 B2 | 4/2012 | Yan et al. |
| 8,192,696 B2 | 6/2012 | Gurski et al. |
| 8,207,362 B2 | 6/2012 | Morris |
| 8,227,371 B2 | 7/2012 | Holtcamp et al. |
| 8,227,635 B2 | 7/2012 | Bowden et al. |
| 8,237,003 B2 | 8/2012 | Holtcamp et al. |
| 8,293,181 B2 | 10/2012 | Saita et al. |
| 8,309,055 B2 | 11/2012 | Arstad et al. |
| 8,324,334 B2 | 12/2012 | Jones et al. |
| 8,324,413 B2 | 12/2012 | O'Rear |
| 8,334,396 B2 | 12/2012 | Papadogianakis et al. |
| 2003/0055184 A1 | 3/2003 | Song et al. |
| 2003/0135080 A1 | 7/2003 | Botha et al. |
| 2003/0236175 A1 | 12/2003 | Twu et al. |
| 2005/0070750 A1 | 3/2005 | Newman et al. |
| 2005/0080301 A1 | 4/2005 | Maughon et al. |
| 2005/0154221 A1 | 7/2005 | Lysenko et al. |
| 2005/0203324 A1 | 9/2005 | Lee et al. |
| 2006/0042158 A1 | 3/2006 | Lee |
| 2006/0047176 A1 | 3/2006 | Gartside et al. |
| 2006/0069274 A1 | 3/2006 | Dias De Moraes E Silva et al. |
| 2006/0167326 A1 | 7/2006 | Burdett et al. |
| 2007/0011943 A1 | 1/2007 | Lin |
| 2007/0151146 A1 | 7/2007 | Lee et al. |
| 2007/0179302 A1 | 8/2007 | Olivier-Bourbigou et al. |
| 2007/0208206 A1 | 9/2007 | Obrecht et al. |
| 2007/0217965 A1 | 9/2007 | Johnson et al. |
| 2007/0225536 A1 | 9/2007 | Lutz |
| 2007/0227400 A1 | 10/2007 | Zullo et al. |
| 2007/0277430 A1 | 12/2007 | Jackman et al. |
| 2008/0047194 A1 | 2/2008 | Prawoto |
| 2008/0097114 A1 | 4/2008 | Bakshi |
| 2008/0103346 A1 | 5/2008 | Burdett et al. |
| 2008/0115407 A1 | 5/2008 | Hoffman |
| 2008/0119664 A1 | 5/2008 | Sinoncelli et al. |
| 2008/0202021 A1 | 8/2008 | Powell |
| 2008/0228017 A1 | 9/2008 | Burdett et al. |
| 2008/0229654 A1 | 9/2008 | Bradin |
| 2008/0244962 A1 | 10/2008 | Abhari et al. |
| 2008/0282606 A1 | 11/2008 | Plaza et al. |
| 2008/0300434 A1 | 12/2008 | Cortright et al. |
| 2008/0306230 A1 | 12/2008 | Pan et al. |
| 2009/0038209 A1 | 2/2009 | Farid et al. |
| 2009/0048459 A1 | 2/2009 | Tupy et al. |
| 2009/0069516 A1 | 3/2009 | Obrecht et al. |
| 2009/0112007 A1 | 4/2009 | Lin et al. |
| 2009/0143544 A1 | 6/2009 | Lysenko et al. |
| 2009/0145022 A1 | 6/2009 | Ng et al. |
| 2009/0163731 A1 | 6/2009 | Martin et al. |
| 2009/0165366 A1 | 7/2009 | Jovanovic et al. |
| 2009/0178330 A1 | 7/2009 | Lebron Parejo et al. |
| 2009/0183420 A1 | 7/2009 | Cobb |
| 2009/0203860 A1 | 8/2009 | Bergbreiter et al. |
| 2009/0264672 A1 | 10/2009 | Abraham et al. |
| 2009/0287004 A1 | 11/2009 | Bergman et al. |
| 2009/0306441 A1 | 12/2009 | Basset et al. |
| 2009/0307966 A1 | 12/2009 | Yan et al. |
| 2009/0324514 A1 | 12/2009 | Awad |
| 2009/0326295 A1 | 12/2009 | Krupa et al. |
| 2010/0010246 A1 | 1/2010 | Yan et al. |
| 2010/0018902 A1 | 1/2010 | Brownscombe et al. |
| 2010/0022789 A1 | 1/2010 | Mignani et al. |
| 2010/0037667 A1 | 2/2010 | Calderon et al. |
| 2010/0043280 A1 | 2/2010 | Morris |
| 2010/0047499 A1 | 2/2010 | Braksmayer et al. |
| 2010/0087671 A1 | 4/2010 | Lemke |
| 2010/0093944 A1 | 4/2010 | Müller et al. |
| 2010/0094034 A1 | 4/2010 | Kaido et al. |
| 2010/0107474 A1 | 5/2010 | Talwar et al. |
| 2010/0113719 A1 | 5/2010 | Patton et al. |
| 2010/0121087 A1 | 5/2010 | Banavali et al. |
| 2010/0130769 A1 | 5/2010 | Banavali et al. |
| 2010/0132252 A1 | 6/2010 | Nakazono |
| 2010/0140136 A1 | 6/2010 | Spilker et al. |
| 2010/0160506 A1 | 6/2010 | Wu et al. |
| 2010/0163459 A1 | 7/2010 | Odueyungbo |
| 2010/0166620 A1 | 7/2010 | Gurski et al. |
| 2010/0167910 A1 | 7/2010 | Odueyungbo |
| 2010/0191008 A1 | 7/2010 | Olson |
| 2010/0212219 A1 | 8/2010 | Siochi et al. |
| 2010/0212220 A1 | 8/2010 | Tirmizi |
| 2010/0223842 A1 | 9/2010 | Thesz et al. |
| 2010/0228042 A1 | 9/2010 | Chun et al. |
| 2010/0234625 A1 | 9/2010 | Papadogianakis et al. |
| 2010/0236984 A1 | 9/2010 | Brookhart et al. |
| 2010/0242348 A1 | 9/2010 | Chen et al. |
| 2010/0243961 A1 | 9/2010 | Hilton et al. |
| 2010/0252485 A1 | 10/2010 | Soane et al. |
| 2010/0263263 A1 | 10/2010 | O'Rear |
| 2010/0264015 A1 | 10/2010 | Portnoff et al. |
| 2010/0282467 A1 | 11/2010 | Hutchison et al. |
| 2010/0305354 A1 | 12/2010 | DuBois |
| 2010/0307051 A1 | 12/2010 | Tremblay et al. |
| 2010/0312012 A1 | 12/2010 | Hannen et al. |
| 2010/0331558 A1 | 12/2010 | Kao et al. |
| 2011/0015419 A1 | 1/2011 | Pendleton et al. |
| 2011/0015434 A1 | 1/2011 | Hannen et al. |
| 2011/0077360 A1 | 3/2011 | Obrecht et al. |
| 2011/0113679 A1 | 5/2011 | Cohen et al. |
| 2011/0160472 A1 | 6/2011 | Lemke et al. |
| 2011/0190524 A1 | 8/2011 | Winde et al. |
| 2011/0198535 A1 | 8/2011 | Meier et al. |
| 2011/0237850 A1 | 9/2011 | Luetkens, Jr. et al. |
| 2011/0252696 A1 | 10/2011 | Franklin et al. |
| 2011/0313180 A1 | 12/2011 | Uptain et al. |
| 2012/0009133 A1 | 1/2012 | Leonard et al. |
| 2012/0035392 A1 | 2/2012 | Kobayashi et al. |
| 2012/0077235 A1 | 3/2012 | Olson |
| 2012/0088943 A1 | 4/2012 | Knuuttila et al. |
| 2012/0116138 A1 | 5/2012 | Goodall et al. |
| 2012/0152723 A1 | 6/2012 | Yoneya |
| 2012/0165293 A1 | 6/2012 | Yiannikouros et al. |
| 2012/0165589 A1 | 6/2012 | Partington |
| 2012/0171090 A1 | 7/2012 | Chang |
| 2012/0178913 A1 | 7/2012 | Lin et al. |
| 2012/0190806 A1 | 7/2012 | Jakel et al. |

(56) References Cited

U.S. PATENT DOCUMENTS

| | | | |
|---|---|---|---|
| 2012/0197031 A1 | 8/2012 | Firth et al. | |
| 2012/0197032 A1 | 8/2012 | Firth et al. | |
| 2012/0271019 A1 | 10/2012 | Drozdak | |
| 2012/0289729 A1 | 11/2012 | Holtcamp et al. | |
| 2012/0329941 A1 | 12/2012 | Ong et al. | |
| 2013/0085288 A1 | 4/2013 | Snead et al. | |

FOREIGN PATENT DOCUMENTS

| | | |
|---|---|---|
| EP | 1 728 844 A1 | 12/2006 |
| JP | 5-4938 A | 1/1993 |
| WO | WO 01/36368 A2 | 5/2001 |
| WO | WO 01/83097 A2 | 11/2001 |
| WO | WO 02/10114 A2 | 2/2002 |
| WO | WO 02/076920 A1 | 10/2002 |
| WO | WO 02/083742 A2 | 10/2002 |
| WO | WO 2004/037754 A2 | 5/2004 |
| WO | WO 2006/043281 A1 | 4/2006 |
| WO | WO 2006/052688 A2 | 5/2006 |
| WO | WO 2006/076364 A2 | 7/2006 |
| WO | WO 2007/027669 A1 | 3/2007 |
| WO | WO 2007/027955 A2 | 3/2007 |
| WO | WO 2007/081987 A2 | 7/2007 |
| WO | WO 2007/092632 A2 | 8/2007 |
| WO | WO 2007/103460 A2 | 9/2007 |
| WO | WO 2007/113530 A2 | 10/2007 |
| WO | WO 2008/046106 A2 | 4/2008 |
| WO | WO 2008/048520 A2 | 4/2008 |
| WO | WO 2008/048522 A1 | 4/2008 |
| WO | WO 2008/058664 A1 | 5/2008 |
| WO | WO 2008/063322 A2 | 5/2008 |
| WO | WO 2008/104929 A1 | 9/2008 |
| WO | WO 2008/152371 A1 | 12/2008 |
| WO | WO 2009/007234 A1 | 1/2009 |
| WO | WO 2009/020665 A1 | 2/2009 |
| WO | WO 2009/020667 A1 | 2/2009 |
| WO | WO 2009/065229 A1 | 5/2009 |
| WO | WO 2009/089591 A1 | 7/2009 |
| WO | WO 2010/021740 A1 | 2/2010 |
| WO | WO 2010/051268 A1 | 5/2010 |
| WO | WO 2010/062958 A1 | 6/2010 |
| WO | WO 2010/074738 A1 | 7/2010 |
| WO | WO 2010/096549 A2 | 8/2010 |
| WO | WO 2010/097519 A2 | 9/2010 |
| WO | WO 2010/104844 A2 | 9/2010 |
| WO | WO 2010/124030 A1 | 10/2010 |
| WO | WO 2010/129051 A1 | 11/2010 |
| WO | WO 2011/046872 A2 | 4/2011 |
| WO | WO 2011/149789 A1 | 12/2011 |
| WO | WO 2012/004489 A1 | 1/2012 |
| WO | WO 2012/129479 A2 | 9/2012 |

OTHER PUBLICATIONS

Schrock et al., "Molybdenum and Tungsten Imido Alkylidene Complexes as Efficient Olefin-Metathesis Catalysts" Angew. Chem. Int. Ed., 42, 2003, pp. 4592-4633.

Schrock, "Recent Advances in High Oxidation State Mo and W Imido Alkylidene Chemistry" Chem. Rev., 109, 2009, pp. 3211-3226.

International Search Report and Written Opinion of the International Searching Authority issued in corresponding PCT Patent Application No. PCT/US2013/063861, mailed Mar. 24, 2014, 12 pages.

Rybak et al., "Cross-metathesis of fatty acid derivatives with methyl acrylate: renewable raw materials for the chemical industry" Green Chem, 9, 2007, pp. 1356-1361.

Forman et al., "Improved cross-metathesis of acrylate esters catalyzed by $2^{nd}$ generation ruthenium carbine complexes" Journal of Organometallic Chemistry, 690, 2005, pp. 5863-5866.

Ahn, Y.M. et al., "A Convenient Method for the Efficient Removal of Ruthenium Byproducts Generated during Olefin Metathesis Reactions," Org. Lett., 2001, vol. 3, pp. 1411-1413.

Boelhouwer et al., "Metathesis of Fatty Acid Esters," JAOCS, vol. 61(2), Feb. 1984, pp. 425-429.

Bourgeois, Damien et al., "The $Cl_2(PCy3)(IMes)Ru(=CHPh)$ catalyst: olefin metathesis versus olefin isomerization," Journal of Organic Metallic Chemistry, vol. 643-644, 2002, pp. 247-252.

Cho, J.H. et al., "An Efficient Method for Removal of Ruthenium Byproucts from Olefin Metathesis Reactions," Org. Lett., 2003, vol. 5, pp. 531-533.

Cotton, F.A. et al., Advanced Inorganic Chemistry, Fifth Edition, New York, John Wiley & Sons, 1988, pp. 382-443.

Formentin, P. et al., "Reactivity of Grubbs' Catalysts with Urea- and Amide-Substituted Olefins. Metathesis and Isomerization," J. Org. Chem., 2005, vol. 70, pp. 8235-8238.

Galan, B. R. et al., "A Rapid and Simple Cleanup Procedure for Metathesis Reactions," Org. Lett., 2007, vol. 9, pp. 1203-1206.

Gimeno, N. et al., "Phenylphosphoric Acid as a New Additive to Inhibit Olefin Isomerization in Ruthenium-Catalyzed Metathesis Reactions," Eur. J. Org. Chem., 2007, pp. 918-924.

Hong, S.H. et al., "Prevention of Undesirable Isomerization During Olefin Metathesis," J. Am. Chem. Soc., 2005, vol. 127, pp. 17160-17161.

James, B.R. et al., "Developments in the Chemistry of Tris(hydroxymehtyl)phosphine," Coordination Chemistry Reviews, 2010, vol. 254, pp. 420-430.

Knight, D.W. et al., "A Simple Oxidative Procedure for the Removal of Ruthenium Residues from Metathesis Reaction Products," Tetrahedron Letters, 2010, vol. 51, pp. 638-640.

Maynard et al., "Purification Technique for the Removal of Ruthenium from Olefin Metathesis Reaction Products," Tetrahedron Letters, vol. 40, No. 22, 1999, pp. 4137-4140.

McEleney, K. et al., "Functionalized Mesoporous Silicates for the Removal of Ruthenium from Reaction Mixtures," Org. Lett., 2006, vol. 8, pp. 2663-2666.

Paquette, L.A. et al., "A Convenient Method for Removing All Highly-Colored Byproducts Generated During Olefin Metathesis Reactions," Org. Lett., 2000, vol. 2, pp. 1259-1261.

Pederson, R.L. et al., "Applications of Olefin Cross Metathesis to Commercial Products," Advanced Synthesis & Catalysts, 2002, vol. 344, pp. 728-735.

Sakamuri, Raj, "Ester," Kirk-Othmer Encyclopedia of Chemical Technology, John Wiley & Sons, 2001, available online Dec. 19, 2003, 31 pages.

Seador, J.D. et al., "Distillation," Perry's Chemical Engineer's Handbook, R.H. Perry and D.W. Green, eds., McGraw-Hill, 7th Ed., 1997, available online Mar. 1, 2001, 7 pages.

Wang, H. et al., "Development of a Robust Ring-Closing Metathesis Reaction in the Synthesis of SB-462795, a Cathepsin K Inhibitor," Organic Process Research & Development, 2008, vol. 12, pp. 226-234.

Warwel, Siegfried et al., "Synthesis of Dicarboxylic Acids by Transition-Metal Catalyzed Oxidative Cleavage of Terminal-Unsaturated Fatty Acids," Topics in Current Chemistry, vol. 164, 1993, 20 pages.

Warwel, V.S., et al., "Metathese ungesättigter Fettsäureester—ein einfacher Zugang zu langkettigen Dicarbonsäuren," Pat Sci. Technol., 94, Nr. 9, 1992, pp. 323-328.

Mol, J.C., "Metathesis of Unsaturated Fatty Acid Esters and Fatty Oils," Journal of Molecular Catalysis 90, 1994, pp. 185-199.

Mol, J.C., "Catalytic Metathesis of Unsaturated Fatty Acid Esters and Oils," Topics in Catalysis, vol. 27, Nos. 1-4, Feb. 2004, pp. 97-104.

Patel, Jim, et al., "Cross-Metathesis of Unsaturated Natural Oils With 2-Butene. High Conversion and Productive Catalyst Turnovers," Chem. Commun., 2005, pp. 5546-5547.

Othmer, Kirk, "Metathesis," Encyclopedia of Chemical Technology, vol. 26, Dec. 2005, pp. 920-958.

International Preliminary Report on Patentability issued in PCT Patent Application No. PCT/US2012/070255, mailed Jul. 3, 2014, 8 pages.

International Preliminary Report on Patentability issued in PCT Patent Application No. PCT/US2012/070275, mailed Jul. 3, 2014, 8 pages.

International Search Report and Written Opinion of the International Searching Authority issued in PCT Patent Application No. PCT/US2014/023530, mailed May 27, 2014, 11 pages.

Ackman, R.G. et al., "Ozonolysis of Unsaturated Fatty Acids," Can. J. Chem., vol. 39, 1961, pp. 1956-1963.

(56) References Cited

OTHER PUBLICATIONS

Throckmorton, P.E. et al., "Pilot Run, Plant Design and Cost Analysis for Reductive Ozonolysis of Methyl Soyate," *Research and Development Laboratories*, 1967, p. 643.

Throckmorton, P.E. et al., "Reductive Ozonolysis of Soybean Oil: Laboratory Optimization of Process Variables," *Research and Development Laboratories*, p. 641, 1967.

Foglia, T.A., et al., "Oxidation of Unsaturated Fatty Acids With Ruthenium and Osmium Tetroxide," *J. Am. Oil Chemists' Soc.*, vol. 54, Nov. 1977, pp. 870A-872A.

Rüsch gen. Klaas, M., et al., "Transition-Metal Catalyzed Oxidative Cleavage of Unsaturated Fatty Acids," *Fat Sci. Technol.*, vol. 95(10), 1995, pp. 359-367.

Turnwald, S.E., et al., "Oleic Acid Oxidation Using Hydrogen Peroxide in Conjunction With Transition Metal Catalysis," *Journal of Materials Science Letters*, vol. 17, 1998, pp. 1305-1307.

Oakley, Michael A., et al., "Practical Dihydroxylation and C-C Cleavage of Unsaturated Fatty Acids," *Journal of Molecular Catalysis A: Chemical*, vol. 150, 1999, pp. 105-111.

Noureddini, H. et al., "Liquid-Phase Catalytic Oxidation of Unsaturated Fatty Acids," *Journal of American Oil Chemists' Society*, vol. 76, No. 3, 1999, pp. 305-312.

Santacesaria, E., et al., "Oxidative Cleavage of the Double Bond of Monoenic Fatty Chains in Two Steps: A New Promising Route to Azelaic Acid and Other Industrial Products," *Ind. Eng. Chem. Res.*, vol. 39, 2000, pp. 2766-2771.

Santacesaria, E. et al., "Double Bond Oxidative Cleavage of Monoenic Fatty Chains," *Catalysis Today*, vol. 79-80, 2003, pp. 59-65.

Bryan, Tom, "Adsorbing It All," *Biodiesel Magazine*, Mar. 2005, pp. 40-43.

Patel, Jim et al., "High Conversion and Productive Catalyst Turnovers in Cross-Metathesis Reactions of Natural Oils With 2-Butene," *Green Chem.*, vol. 8, 2006, pp. 450-454.

Kram, Jerry W., "Cleaner and Clearer," *Biodiesel Magazine*, Jan. 2008, 4 pages.

International Search Report and Written Opinion of the International Searching Authority for International Application No. PCT/US2010/052174, dated Apr. 15, 2011, 9 pages.

METHODS OF REFINING AND PRODUCING DIBASIC ESTERS AND ACIDS FROM NATURAL OIL FEEDSTOCKS

CROSS REFERENCE TO RELATED APPLICATIONS

This application is a continuation-in-part application of U.S. patent application Ser. No. 12/901,829, filed Oct. 11, 2010, which claims the benefit of U.S. Provisional Patent Application No. 61/250,743, filed Oct. 12, 2009, the disclosures of which are incorporated herein by reference.

GOVERNMENT RIGHTS

This invention was made with Government support under grant no. DE-EE0002872/001 awarded by the Department of Energy. The U.S. Government has certain rights in this invention.

BACKGROUND

Metathesis is a catalytic reaction generally known in the art that involves the interchange of alkylidene units among compounds containing one or more double bonds (e.g., olefinic compounds) via the formation and cleavage of the carbon-carbon double bonds. Metathesis may occur between two like molecules (often referred to as self-metathesis) and/or it may occur between two different molecules (often referred to as cross-metathesis). Self-metathesis may be represented schematically as shown in Equation I.

$$R^1-CH=CH-R^2 + R^1-CH=CH-R^2$$
$$\leftrightarrow R^1-CH=CH-R^1 + R^2-CH=CH-R^2 \quad (I)$$

wherein $R^1$ and $R^2$ are organic groups.

Cross-metathesis may be represented schematically as shown in Equation II.

$$R^1-CH=CH-R^2 + R^3-CH=CH-R^4$$
$$\leftrightarrow R^1-CH=CH-R^3 + R^1-CH=CH-R^4 +$$
$$R^2-CH=CH-R^3 + R^2-CH=CH-R^4 + R^1-$$
$$CH=CH-R^1 + R^2-CH=CH-R^2 + R^3-$$
$$CH=CH-R^3 + R^4-CH=CH-R^4 \quad (II)$$

wherein $R^1$, $R^2$, $R^3$, and $R^4$ are organic groups.

In recent years, there has been an increased demand for environmentally friendly techniques for manufacturing materials typically derived from petroleum sources. For example, researchers have been studying the feasibility of manufacturing biofuels, waxes, plastics, and the like, using natural oil feedstocks, such as vegetable and seed-based oils. In one non-limiting example, metathesis catalysts are used to manufacture candle wax, as described in PCT/US2006/000822, which is herein incorporated by reference in its entirety. Metathesis reactions involving natural oil feedstocks offer promising solutions for today and for the future.

Natural oil feedstocks of interest include non-limiting examples such as natural oils (e.g., vegetable oils, fish oil, animal fats) and derivatives of natural oils, such as fatty acids and fatty acid alkyl (e.g., methyl) esters. These feedstocks may be converted into industrially useful chemicals (e.g., waxes, plastics, cosmetics, biofuels, etc.) by any number of different metathesis reactions. Significant reaction classes include, as non-limiting examples, self-metathesis, cross-metathesis with olefins, and ring-opening metathesis reactions. Representative non-limiting examples of useful metathesis catalysts are provided below. Metathesis catalysts can be expensive and, therefore, it is desirable to improve the efficiency of the metathesis catalyst.

In recent years, there has been an increased demand for petroleum-based transportation fuels. Concerns exist that the world's petroleum production may not be able to keep up with demand. Additionally, the increased demand for petroleum-based fuels has resulted in a higher production of greenhouse gases. In particular, the airline industry accounts for greater than 10% of the greenhouse gases within the United States. Due to the increased demand for fuel and increased production of greenhouse gases, there is a need to explore methods of producing environmentally-friendly, alternative fuel sources. In particular, there is a need to explore methods of producing environmentally friendly fuel compositions and specialty chemicals from a natural feedstock.

BRIEF SUMMARY

Methods are disclosed for refining a natural oil feedstock through a metathesis reaction of the natural oil feedstock in the presence of a metathesis catalyst.

In one embodiment, the method comprises forming dibasic acids or dibasic esters by reacting a feedstock comprising a natural oil in the presence of a metathesis catalyst under conditions sufficient to form a metathesized product, wherein the metathesized product comprises olefins and esters. The method further comprises separating the olefins in the metathesized product from the esters in the metathesized product. The method further comprises transesterifying the esters in the presence of an alcohol to form a transesterified product comprising a terminal olefin ester having the following structure:

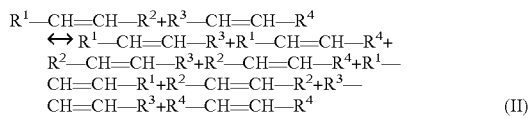

wherein X is a $C_3$-$C_{18}$ saturated or unsaturated alkyl chain, and R is an alkyl group. The method further comprises reacting the terminal olefin ester with an internal olefin ester in the presence of a second metathesis catalyst to form a dibasic ester.

In certain embodiments, R is methyl. In some embodiments, the weight ratio of the terminal olefin to the internal olefin is between 5:1 and 1:5. In other embodiments, the weight ratio of the terminal olefin to the internal olefin is 1:1.

In some embodiments, the terminal olefin ester is selected from the group consisting of: 4-pentenoic acid ester, 5-hexenoic acid ester, 6-heptenoic acid ester, 7-octenoic acid ester, 8-nonenoic acid ester, 9-decenoic acid ester, 10-undecenoic acid ester, 11-dodecenoic acid ester, 12-tridecenoic acid ester, 13-tetradecenoic acid ester, 14-pentadecenoic acid ester, 15-hexadecenoic acid ester, 16-heptadecenoic acid ester, 17-octadecenoic acid ester, and mixtures thereof. In one particular embodiment, the terminal olefin ester is 9-decenoic acid ester. In certain embodiments, the internal olefin ester is selected from the group consisting of: pentenoic acid esters, hexenoic acid esters, heptenoic acid esters, octenoic acid esters, nonenoic acid esters, decenoic acid esters, undecenoic acid esters, dodecenoic acid esters, tridecenoic acid esters, tetradecenoic acid esters, pentadecenoic acid esters, hexadecenoic acid esters, heptadecenoic acid esters, octadecenoic acid esters, and mixtures thereof. In one particular embodiment, the internal olefin ester is 9-dodecenoic acid ester.

In some embodiments, the internal olefin ester is formed by reacting a portion of the terminal olefin ester from the transesterified product with a low-molecular-weight internal olefin or a mid-weight internal olefin in the presence of a metathesis catalyst. In certain embodiments, the low-molecular-weight internal olefin is selected from the group consisting of: 2-butene, 2-pentene, 2-hexene, 3-hexene, 2-heptene, 3-heptene, 2-octene, 3-octene, 4-octene, 2-nonene, 3-nonene, 4-nonene, and mixtures thereof. In one particular embodiment, the low-molecular-weight internal olefin is 3-hexene.

In some embodiments, the dibasic acid formed is 9-octadecene dioic acid dimethyl ester. In some embodiments, the dibasic ester may undergo a hydrolysis reaction with water to form a dibasic acid. In one embodiment, 9-octadecene dioic acid methyl ester is hydrolyzed to form 9-octadecene dioic acid.

In another embodiment, the method comprises reacting a feedstock comprising a natural oil in the presence of a metathesis catalyst under conditions sufficient to form a metathesized product, wherein the metathesized product comprises olefins and esters. The method further comprises separating the olefins in the metathesized product from the esters in the metathesized product. The method further comprises transesterifying the esters in the presence of an alcohol to form a transesterified product comprising 9 decenoic acid ester. The method further comprises reacting the 9-decenoic acid ester with 9-dodecenoic acid ester in the presence of a second metathesis catalyst to form 9-octadecene dioic acid ester.

In certain embodiments, the 9-dodecenoic acid ester is formed by reacting a portion of the 9-decenoic acid ester with a low-molecular-weight internal olefin or a mid-weight internal olefin in the presence of a third metathesis catalyst. In one embodiment, the low-molecular-weight internal olefin is 3-hexene.

In some embodiments, the 9-octadecene dioic acid ester is hydrolyzed to form 9-octadecene dioic acid.

DETAILED DESCRIPTION

Figure 1:
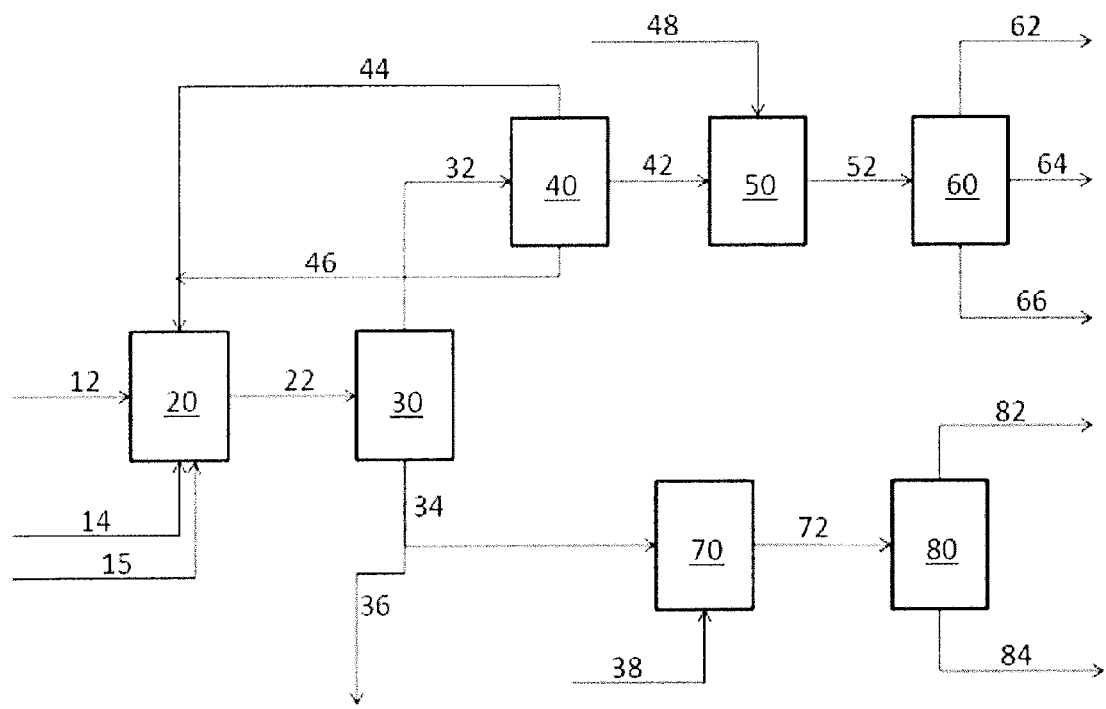
FIG. 1 is a schematic diagram of one embodiment of a process to produce a fuel composition and a transesterified product from a natural oil.

As used herein, the singular forms "a," "an," and "the" include plural referents unless the context clearly dictates otherwise. For example, reference to "a substituent" encompasses a single substituent as well as two or more substituents, and the like.

As used herein, the terms "for example," "for instance," "such as," or "including" are meant to introduce examples that further clarify more general subject matter. Unless otherwise specified, these examples are provided only as an aid for understanding the applications illustrated in the present disclosure, and are not meant to be limiting in any fashion.

As used herein, the following terms have the following meanings unless expressly stated to the contrary. It is understood that any term in the singular may include its plural counterpart and vice versa.

As used herein, the term "metathesis catalyst" includes any catalyst or catalyst system that catalyzes a metathesis reaction.

As used herein, the terms "natural oils," "natural feedstocks," or "natural oil feedstocks" may refer to oils derived from plants or animal sources. The term "natural oil" includes natural oil derivatives, unless otherwise indicated. Examples of natural oils include, but are not limited to, vegetable oils, algae oils, fish oils, animal fats, tall oils, derivatives of these oils, combinations of any of these oils, and the like. Representative non-limiting examples of vegetable oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, pennycress oil, camelina oil, and castor oil. Representative non-limiting examples of animal fats include lard, tallow, poultry fat, yellow grease, and fish oil. Tall oils are by-products of wood pulp manufacture.

As used herein, the term "natural oil derivatives" may refer to the compounds or mixture of compounds derived from the natural oil using any one or combination of methods known in the art. Such methods include but are not limited to saponification, fat splitting, transesterification, esterification, hydrogenation (partial or full), isomerization, oxidation, and reduction. Representative non-limiting examples of natural oil derivatives include gums, phospholipids, soapstock, acidulated soapstock, distillate or distillate sludge, fatty acids and fatty acid alkyl ester (e.g. non-limiting examples such as 2-ethylhexyl ester), hydroxy substituted variations thereof of the natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (i.e., RBD soybean oil). Soybean oil typically comprises about 95% weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9,12-octadecadienoic acid), and linolenic acid (9,12,15-octadecatrienoic acid).

As used herein, the term "low-molecular-weight olefin" may refer to any one or combination of unsaturated straight, branched, or cyclic hydrocarbons in the $C_2$ to $C_{14}$ range. Low-molecular-weight olefins include "alpha-olefins" or "terminal olefins," wherein the unsaturated carbon-carbon bond is present at one end of the compound. Low-molecular-weight olefins may also include dienes or trienes. Low-molecular-weight olefins may also include internal olefins or "low-molecular-weight internal olefins." In certain embodiments, the low-molecular-weight internal olefin is in the $C_4$ to $C_{14}$ range. Examples of low-molecular-weight olefins in the $C_2$ to $C_6$ range include, but are not limited to: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. Non-limiting examples of low-molecular-weight olefins in the $C_7$ to $C_9$ range include 1,4-heptadiene, 1-heptene, 3,6-nonadiene, 3-nonene, 1,4,7-octatriene. Other possible low-molecular-weight olefins include styrene and vinyl cyclohexane. In certain embodiments, it is preferable to use a mixture of olefins, the mixture comprising linear and branched low-molecular-weight olefins in the $C_4$-$C_{10}$ range. In one embodiment, it may be preferable to use a mixture of linear and branched $C_4$ olefins (i.e., combinations of: 1-butene, 2-butene, and/or isobutene). In other embodiments, a higher range of $C_{11}$-$C_{14}$ may be used.

As used herein, the term "mid-weight olefin" may refer to any one or combination of unsaturated straight, branched, or cyclic hydrocarbons in the $C_{15}$ to $C_{24}$ range. Mid-weight olefins include "alpha-olefins" or "terminal olefins," wherein the unsaturated carbon-carbon bond is present at one end of the compound. Mid-weight olefins may also include dienes or trienes. Mid-weight olefins may also include internal olefins or "mid-weight internal olefins." In certain embodiments, it is preferable to use a mixture of olefins.

As used herein, the terms "metathesize" and "metathesizing" may refer to the reacting of a feedstock in the presence of a metathesis catalyst to form a "metathesized product" comprising a new olefinic compound. Metathesizing may refer to cross-metathesis (a.k.a. co-metathesis), self-metathesis, ring-opening metathesis, ring-opening metathesis polymerizations ("ROMP"), ring-closing metathesis ("RCM"), and acyclic diene metathesis ("ADMET"). As a non-limiting example, metathesizing may refer to reacting two triglycerides present in a natural feedstock (self-metathesis) in the presence of a metathesis catalyst, wherein each triglyceride has an unsaturated carbon-carbon double bond, thereby forming a new mixture of olefins and esters which may include a triglyceride dimer. Such triglyceride dimers may have more than one olefinic bond, thus higher oligomers also may form. Additionally, metathesizing may refer to reacting an olefin, such as ethylene, and a triglyceride in a natural feedstock having at least one unsaturated carbon-carbon double bond, thereby forming new olefinic molecules as well as new ester molecules (cross-metathesis).

As used herein, the terms "ester" and "esters" may refer to compounds having the general formula: R—COO—R', wherein R and R' denote any organic compound (such as alkyl, aryl, or silyl groups), including those bearing heteroatom containing substituent groups. In certain embodiments, R and R' denote alkyl or aryl groups. In certain embodiments, the term "ester" or "esters" may refer to a group of compounds with the general formula described above, wherein the compounds have different carbon lengths.

As used herein, the term "dibasic ester" may refer to compounds having the general formula R'—OOC—Y—COO—R", wherein Y, R', and R" denote any organic compound (such as alkyl, aryl, or silyl groups), including those bearing heteroatom containing substituent groups. In certain embodiments, Y is a saturated or unsaturated hydrocarbon, and R' and R" are alkyl or aryl groups.

As used herein, the term "dibasic acid" may refer to compounds having the general formula R'—OOC—Y—COO—R", wherein R' and R" are hydrogen, and Y denotes any organic compound (such as an alkyl, aryl, or silyl group), including those bearing heteroatom substituent groups. In certain embodiments, Y is a saturated or unsaturated hydrocarbon.

As used herein, the terms "olefin" and "olefins" may refer to hydrocarbon compounds having at least one unsaturated carbon-carbon double bond. In certain embodiments, the term "olefin" or "olefins" may refer to a group of unsaturated carbon-carbon double bond compounds with different carbon lengths.

It is noted that an olefin may also comprise an ester, and an ester may also comprise an olefin, if the R or R' group in the general formula R—COO—R' contains an unsaturated carbon-carbon double bond. For example, a "terminal olefin ester" may refer to an ester compound where R has an olefin positioned at the end of the chain. An "internal olefin ester" may refer to an ester compound where R has an olefin positioned at an internal location on the chain. Additionally, the term "terminal olefin" may refer to an ester or an acid thereof where R' denotes hydrogen or any organic compound (such as an alkyl, aryl, or silyl group) and R has an olefin positioned at the end of the chain, and the term "internal olefin" may refer to an ester or an acid thereof where R' denotes hydrogen or any organic compound (such as an alkyl, aryl, or silyl group) and R has an olefin positioned at an internal location on the chain.

As used herein, the terms "paraffin" and "paraffins" may refer to hydrocarbon compounds having only single carbon-carbon bonds, having the general formula $C_nH_{2n+2}$, where, in certain embodiments, n is greater than about 20.

As used herein, the terms "isomerization," "isomerizes," or "isomerizing" may refer to the reaction and conversion of straight-chain hydrocarbon compounds, such as normal paraffins, into branched hydrocarbon compounds, such as iso-paraffins. In other embodiments, the isomerization of an olefin or an unsaturated ester indicates the shift of the carbon-carbon double bond to another location in the molecule (e.g., conversion from 9-decenoic acid to 8-decenoic acid), or it indicates a change in the geometry of the compound at the carbon-carbon double bond (e.g., cis to trans). As a non-limiting example, n-pentane may be isomerized into a mixture of n-pentane, 2-methylbutane, and 2,2-dimethylpropane. Isomerization of normal paraffins may be used to improve the overall properties of a fuel composition. Additionally, isomerization may refer to the conversion of branched paraffins into further, more branched paraffins.

As used herein, the term "yield" may refer to the total weight of fuel produced from the metathesis and hydrogenation reactions. It may also refer to the total weight of the fuel following a separation step and/or isomerization reaction. It may be defined in terms of a yield %, wherein the total weight of the fuel produced is divided by the total weight of the natural oil feedstock and, in some embodiments, low-molecular-weight olefin and/or mid-weight olefin, combined.

As used herein, the terms "fuels" and "fuel compositions" refer to materials meeting required specifications or to blend components that are useful in formulating fuel compositions but, by themselves, do not meet all of the required specifications for a fuel.

As used herein, the term "jet fuel" or "aviation fuel" may refer to kerosene or naphtha-type fuel cuts, or military-grade jet fuel compositions. "Kerosene-type" jet fuel (including Jet A and Jet A-1) has a carbon number distribution between about 8 and about 16. Jet A and Jet A-1 typically have a flash point of at least approximately 38° C., an auto ignition temperature of approximately 210° C., a freeze point less than or equal to approximately −40° C. for Jet A and −47° C. for Jet A-1, a density of approximately 0.8 g/cc at 15° C., and an energy density of approximately 42.8-43.2 MJ/kg. "Naphtha-type" or "wide-cut" jet fuel (including Jet B) has a carbon number distribution between about 5 and about 15. Jet B typically comprises a flash point below approximately 0° C., an auto ignition temperature of approximately 250° C., a freeze point of approximately −51° C., a density of approximately 0.78 g/cc, and an energy density of approximately 42.8-43.5 MJ/kg. "Military grade" jet fuel refers to the Jet Propulsion or "JP" numbering system (JP-1, JP-2, JP-3, JP-4, JP-5, JP-6, JP-7, JP-8, etc.). Military grade jet fuels may comprise alternative or additional additives to have higher flash points than Jet A, Jet A-1, or Jet B in order to cope with heat and stress endured during supersonic flight.

As used herein, the term "diesel fuel" may refer to a hydrocarbon composition having the following property characteristics, including a carbon number distribution between about 8 and about 25. Diesel fuels also typically have a specific gravity of approximately 0.82-1.08 at 15.6° C. (60° F.), based on water having a specific gravity of 1 at 60° F. Diesel fuels typically comprise a distillation range between approximately 180-340° C. (356-644° F.). Additionally, diesel fuels have a minimum cetane index number of approximately 40.

As used herein, the term "carbon number distribution" may refer to the range of compounds present in a composition, wherein each compound is defined by the number of carbon atoms present. As a non-limiting example, a naphtha-type jet fuel typically comprises a distribution of hydrocarbon compounds wherein a majority of those compounds have between 5 and 15 carbon atoms each. A kerosene-type jet fuel typically comprises a distribution of hydrocarbon compounds wherein a majority of those compounds have between 8 and 16 carbon atoms each. A diesel fuel typically comprises a distribution of hydrocarbon compounds wherein a majority of those compounds have between 8 and 25 carbon atoms each.

As used herein, the term "energy density" may refer to the amount of energy stored in a given system per unit mass (MJ/kg) or per unit volume (MJ/L), where MJ refer to million Joules. As a non-limiting example, the energy density of kerosene- or naphtha-type jet fuel is typically greater than about 40 MJ/kg.

In certain embodiments, dibasic acids and/or dibasic esters and olefin byproducts may be formed by reacting terminal olefins having the following structure:

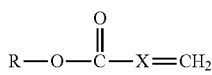

(where X is a $C_3$-$C_{18}$ saturated or unsaturated alkyl chain, and R is an alkyl group or hydrogen) with internal olefins in the presence of a metathesis catalyst. In certain embodiments, the terminal olefin is derived from a natural oil feedstock (described in greater detail below). In other embodiments, the terminal olefin is purchased or produced from an external source separate than those derived from the natural oil feedstock.

In certain embodiments, the terminal olefin-internal olefin cross-metathesis reaction is conducted at a weight ratio between 1:99 (terminal to internal) and 99:1 (terminal to internal). In other embodiments, the weight ratio of the terminal and internal olefin is between 1:5 and 5:1. In yet other embodiments, the weight ratio between the terminal and internal olefin is between 1:2 and 2:1. In one particular embodiment, the weight ratio between the terminal and internal olefin is approximately 1:1.

In certain embodiments, the terminal olefin is selected from the group consisting of: 4-pentenoic acid ester, 5-hexenoic acid ester, 6-heptenoic acid ester, 7-octenoic acid ester, 8-nonenoic acid ester, 9-decenoic acid ester, 10-undecenoic acid ester, 11-dodecenoic acid ester, 12-tridecenoic acid ester, 13-tetradecenoic acid ester, 14-pentadecenoic acid ester, 15-hexadecenoic acid ester, 16-heptadecenoic acid ester, 17-octadecenoic acid ester, acids thereof, and mixtures thereof. In one particular embodiment, the terminal olefin is 9-decenoic acid ester.

In certain embodiments, the internal olefin is selected from the group consisting of: pentenoic acid esters, hexenoic acid esters, heptenoic acid esters, octenoic acid esters, nonenoic acid esters, decenoic acid esters, undecenoic acid esters, dodecenoic acid esters, tridecenoic acid esters, tetradecenoic acid esters, pentadecenoic acid esters, hexadecenoic acid esters, heptadecenoic acid esters, octadecenoic acid esters, acids thereof, and mixtures thereof. In one particular embodiment, the internal olefin is 9-undecenoic acid ester. In another particular embodiment, the internal olefin is 9-dodecenoic acid ester.

In some embodiments, the internal olefin is formed by reacting a portion of the terminal olefin ester with a low-molecular-weight internal olefin or mid-weight internal olefin in the presence of a metathesis catalyst. In certain embodiments, the low-molecular-weight internal olefin is selected from the group consisting of: 2-butene, 2-pentene, 2-hexene, 3-hexene, 2-heptene, 3-heptene, 2-octene, 3-octene, 4-octene, 2-nonene, 3-nonene, 4-nonene, and mixtures thereof. In one particular embodiment, the low-molecular-weight internal olefin is 2-butene. In another particular embodiment, the low-molecular-weight internal olefin is 3-hexene.

This process of cross-metathesizing a terminal olefin with an internal olefin may have certain advantages over a self-metathesis reaction to create a diacid ester or diacid. For example, the cross-metathesis reaction with an internal olefin helps limit the amount of ethylene byproduct formed that can potentially poison various metathesis catalysts. In some instances, this cross-metathesis mechanism allows for mild reaction conditions, lower catalyst usage, higher conversion rates, and reduced olefin isomerization byproduct reactions in comparison to self-metathesis mechanisms.

In certain embodiments, at least 70 wt %, 80 wt %, or 90 wt % dibasic ester and/or dibasic acid is formed from the cross-metathesis reaction of a terminal olefin and an internal olefin in the presence of less than 150 ppm, 100 ppm, 50 ppm, 25 ppm, or 10 ppm catalyst. A comparable self-metathesis reaction with terminal olefins (such as 9-decenoic acid ester) under similar reaction conditions may require more catalyst (e.g., more than 150 ppm, or more than 500 ppm) to achieve similar yields of dibasic esters and/or dibasic acids (potentially due to the formation of the ethylene byproduct).

In certain embodiments, the dibasic ester and/or dibasic acid yield is improved by separating the olefin byproduct formed in the cross-metathesis reaction from the metathesis product while the reaction between the terminal olefin and internal olefin is ongoing. In other embodiments, the dibasic ester and/or dibasic acid yield is improved by sparging the metathesis products in the metathesis reactor with a chemically inert gas (e.g., nitrogen, argon, or helium) to ventilate dissolved gases/byproducts (e.g., olefin byproducts) in the metathesis product.

In certain embodiments, the cross-metathesis reaction of the terminal olefin and internal olefin produces a dibasic ester comprising the following structure:

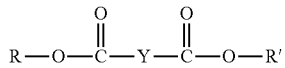

wherein R and R' are independently alkyl, aryl, or silyl groups, and Y is an olefin comprising between 6 and 36 carbon atoms. In one embodiment, the cross-metathesis reaction forms a dibasic ester, where R and R' are methyl and Y is 8-hexadecene (i.e., the dibasic ester formed from the cross-metathesis reaction of a terminal olefin and an internal olefin is dimethyl 9-octadecenedioate).

In some embodiments, the dibasic ester may undergo a hydrolysis reaction with water to form a dibasic acid having the following structure:

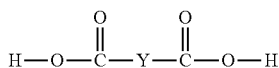

wherein Y is an olefin comprising between 6 and 36 carbon atoms. In one embodiment, Y is 8-hexadecene (i.e., the dibasic acid is 9-octadecene dioic acid). Following hydrolysis, in some embodiments, the product stream may be sent to a flash column or decanter to remove methanol and water from the diacid.

In other embodiments, the dibasic acid and/or dibasic ester is isomerized to form an isomerized dibasic acid and/or isomerized dibasic ester. The isomerization of the dibasic acid and/or dibasic ester may be conducted at an elevated temperature (i.e., greater than 25° C.). In certain embodiments, the temperature of the heat treatment for the isomerization reaction is greater than 100° C., greater than 150° C., or greater than 200° C. In other embodiments, the temperature is between 100° C.-300° C., between 150-250° C., or about 200° C. In some embodiments, the heat treatment step is conducted in the presence of an isomerization catalyst. In one particular embodiment, the isomerization catalyst is $(PCy_3)_2(Cl)(H)Ru(CO)$, where "Cy" represents a cyclohexyl group.

In certain embodiments, the isomerized dibasic acid and/or isomerized dibasic ester comprises compounds selected from the group consisting of: isomerized dimethyl 9-octadecenedioate or isomerized 9-octadecene dioic acid.

In certain embodiments, the isomerized dibasic acid and/or isomerized dibasic ester is self-metathesized or cross-metathesized with a low-molecular-weight olefin or mid-weight olefin. Typical metathesis reaction conditions and catalysts are discussed in greater detail below. In one embodiment, the isomerized dibasic acid and/or isomerized dibasic ester is self-metathesized in the presence of approximately 10 ppm, 20 ppm, 40 ppm, 50 ppm, 80 ppm, 100 ppm, 120 ppm, or greater than 150 ppm metathesis catalyst.

In certain embodiments, the dibasic acid, dibasic ester, isomerized dibasic acid, and/or isomerized dibasic ester is hydrogenated. Typical hydrogenation reaction conditions and catalysts are discussed in greater detail below. In one particular example, the hydrogenation reaction is conducted in the presence of a nickel based catalyst at approximately 150° C. and 150 psig.

In certain embodiments, the dibasic acids, dibasic esters, isomerized dibasic acids, and/or isomerized dibasic esters may be used in a variety of different commercial applications, including, but not limited to: lubricants, waxes, films, paints, paint strippers, coatings, plasticizers, resins, binders, solvents, polyols, soil stabilization, chemical grouting, oilfield drilling fluids, crop protection products, surfactants, intermediates, and adhesives.

As mentioned above, the terminal olefin and internal olefin may be derived from a natural oil feedstock, in addition to other valuable compositions. A number of valuable compositions may be targeted through the self-metathesis reaction of a natural oil feedstock, or the cross-metathesis reaction of the natural oil feedstock with a low-molecular-weight olefin or mid-weight olefin, in the presence of a metathesis catalyst. Such valuable compositions may include fuel compositions, detergents, surfactants, and other specialty chemicals. Non-limiting examples of fuel compositions include jet, kerosene, and diesel fuel. Additionally, transesterified products (i.e., the products formed from transesterifying an ester in the presence of an alcohol) may also be targeted, non-limiting examples of which include: fatty acid methyl esters; biodiesel; 9-decenoic acid ("9DA") esters, 9-undecenoic acid ("9UDA") esters, and/or 9-dodecenoic acid ("9DDA") esters; 9DA, 9UDA, and/or 9DDA; alkali metal salts and alkaline earth metal salts of 9DA, 9UDA, and/or 9DDA; dimers of the transesterified products; and mixtures thereof.

In certain embodiments, prior to a metathesis reaction, a natural oil feedstock may be treated to render the natural oil more suitable for the subsequent metathesis reaction. In certain embodiments, the natural oil preferably is a vegetable oil or vegetable oil derivative, such as soybean oil.

In one embodiment, the treatment of the natural oil involves the removal of catalyst poisons, such as peroxides, which may potentially diminish the activity of the metathesis catalyst. Non-limiting examples of natural oil feedstock treatment methods to diminish catalyst poisons include those described in PCT/US2008/09604, PCT/US2008/09635, and U.S. patent application Ser. Nos. 12/672,651 and 12/672,652, herein incorporated by reference in their entireties. In certain embodiments, the natural oil feedstock is thermally treated by heating the feedstock to a temperature greater than 100° C. in the absence of oxygen and held at the temperature for a time sufficient to diminish catalyst poisons in the feedstock. In other embodiments, the temperature is between approximately 100° C. and 300° C., between approximately 120° C. and 250° C., between approximately 150° C. and 210° C., or approximately between 190 and 200° C.

In one embodiment, the absence of oxygen is achieved by sparging the natural oil feedstock with nitrogen, wherein the nitrogen gas is pumped into the feedstock treatment vessel at a pressure of approximately 10 atm (150 psig).

In certain embodiments, the natural oil feedstock is chemically treated under conditions sufficient to diminish the catalyst poisons in the feedstock through a chemical reaction of the catalyst poisons. In certain embodiments, the feedstock is treated with a reducing agent or a cation-inorganic base composition. Non-limiting examples of reducing agents include bisulfite, borohydride, phosphine, thiosulfate, individually or combinations thereof.

In certain embodiments, the natural oil feedstock is treated with an adsorbent to remove catalyst poisons. In one embodiment, the feedstock is treated with a combination of thermal and adsorbent methods. In another embodiment, the feedstock is treated with a combination of chemical and adsorbent methods. In another embodiment, the treatment involves a partial hydrogenation treatment to modify the natural oil feedstock's reactivity with the metathesis catalyst. Additional non-limiting examples of feedstock treatment are also described below when discussing the various metathesis catalysts.

Additionally, in certain embodiments, the low-molecular-weight olefin or mid-weight olefin may also be treated prior to the metathesis reaction with the natural oil. Like the natural oil treatment, the low-molecular-weight olefin or mid-weight olefin may be treated to remove poisons that may impact or diminish catalyst activity.

In certain embodiments, the low-molecular-weight olefin or mid-weight olefin may be self-metathesized to form a metathesized low-molecular-weight olefin or metathesized mid-weight olefin in order to adjust the properties of the olefin and the potential products following metathesis with the natural oil. In some embodiments, the low-molecular-weight olefin or mid-weight olefin is self-metathesized in the presence of a rhenium oxide catalyst (e.g., rhenium oxide supported on alumina) or tungsten oxide catalyst (e.g., tungsten oxide supported on silica). This reaction may be conducted in a fixed bed reactor. In one embodiment, the low-molecular-weight olefin is 1-butene. The low-molecular-weight olefin may be self-metathesized over rhenium oxide catalyst in a fixed bed reactor to produce mainly 3-hexene and ethylene. Ethylene may be separated from the reactor effluent for further processing, such as being sent to an ethylene purification system or ethylene oxide system. Unreacted low-molecular-weight olefin (e.g., 1-butene) may be recycled to the fixed bed reactor and the metathesized low-weight-olefin (e.g., 3-hexene) may be sent to the metathesis reactor for metathesis with the natural oil.

In other embodiments, the low-molecular-weight olefin or mid-weight olefin is isomerized prior to being metathesized with the natural oil. Adjusting the composition and properties of the low-molecular-weight olefin or mid-weight olefin through isomerization may allow for different products or different ratios of products to be formed following metathesis of the low-molecular-weight olefin or mid-weight olefin with a natural oil. In some embodiments, the isomerized or branched low-molecular-weight olefin is in the $C_4$ to $C_{10}$ range. In one embodiment, hexene is isomerized to form a branched low-molecular-weight olefin. Non-limiting examples of branched low-molecular-weight olefins include isobutene, 3-methyl-1-butene, 2-methyl-3-pentene, and 2,2-dimethyl-3-pentene.

By using branched low-molecular-weight olefins or branched mid-weight olefins in the metathesis reaction, the metathesized product will include branched olefins, which can be subsequently hydrogenated to iso-paraffins. In certain embodiments, the branched low-molecular-weight olefins or branched mid-weight olefins may help achieve the desired performance properties for a fuel composition, such as jet, kerosene, or diesel fuel. In certain embodiments, $C_{11}$-$C_{14}$ olefins may be targeted following metathesis and separation steps through isomerization of the low-molecular-weight olefin. In other embodiments, the branched low-molecular-weight olefins or branched mid-weight olefins may help target longer chain esters for use as detergents or cleaning compositions. In some embodiments, $C_{10}$-$C_{15}$ or $C_{11}$-$C_{14}$ methyl esters may be targeted following metathesis, separation, and transesterification steps (discussed in detail below). Isomerization reactions are well-known in the art, as described in U.S. Pat. Nos. 3,150,205; 4,210,771; 5,095,169; and 6,214,764, herein incorporated by reference in their entireties.

As shown in FIG. 1, after this optional treatment of the natural oil feedstock, low-molecular-weight olefin, and/or mid-weight olefin, the natural oil 12 is reacted with itself, or combined with a low-molecular-weight olefin 14 or mid-weight olefin 15 in a metathesis reactor 20 in the presence of a metathesis catalyst. Metathesis catalysts and metathesis reaction conditions are discussed in greater detail below. In certain embodiments, in the presence of a metathesis catalyst, the natural oil 12 undergoes a self-metathesis reaction with itself. In other embodiments, in the presence of the metathesis catalyst, the natural oil 12 undergoes a cross-metathesis reaction with the low-molecular-weight olefin 14 or mid-weight olefin 15. In certain embodiments, the natural oil 12 undergoes both self- and cross-metathesis reactions in parallel metathesis reactors. The self-metathesis and/or cross-metathesis reaction form a metathesized product 22 wherein the metathesized product 22 comprises olefins 32 and esters 34.

In certain embodiments, the low-molecular-weight olefin 14 is in the $C_2$ to $C_6$ range. As a non-limiting example, in one embodiment, the low-molecular-weight olefin 14 may comprise at least one of the following: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. Non-limiting examples of low-molecular-weight olefins in the $C_7$ to $C_9$ range include 1,4-heptadiene, 1-heptene, 3,6-nonadiene, 3-nonene, 1,4,7-octatriene. In another embodiment, the low-molecular-weight olefin 14 comprises at least one of styrene and vinyl cyclohexane. In another embodiment, the low-molecular-weight olefin 14 may comprise at least one of ethylene, propylene, 1-butene, 2-butene, and isobutene. In another embodiment, the low-molecular-weight olefin 14 comprises at least one alpha-olefin or terminal olefin in the $C_2$ to $C_{10}$ range.

In another embodiment, the low-molecular-weight olefin 14 comprises at least one branched low-molecular-weight olefin in the $C_4$ to $C_{10}$ range. Non-limiting examples of branched low-molecular-weight olefins include isobutene, 3-methyl-1-butene, 2-methyl-3-pentene, and 2,2-dimethyl-3-pentene.

In certain embodiments, the mid-weight olefin 15 comprises unsaturated straight, branched, or cyclic hydrocarbons in the $C_{15}$ to $C_{24}$ range. In some embodiments, the mid-weight olefin is an alpha-olefin or terminal olefin.

As noted, it is possible to use a mixture of various linear or branched low-molecular-weight olefins and linear or branched mid-weight olefins in the reaction to achieve the desired metathesis product distribution. In certain embodiments, the mixture comprises linear and/or branched low-molecular-weight olefins. In other embodiments, the mixture comprises linear and/or branched mid-weight olefins. In one embodiment, a mixture of butenes (1-butene, 2-butenes, and, optionally, isobutene) may be employed as the low-molecular-weight olefin, offering a low cost, commercially available feedstock instead a purified source of one particular butene. Such low cost mixed butene feedstocks are typically diluted with n-butane and/or isobutane.

In certain embodiments, recycled streams from downstream separation units may be introduced to the metathesis reactor 20 in addition to the natural oil 12 and, in some embodiments, the low-molecular-weight olefin 14 and/or mid-weight olefin 15. For instance, in some embodiments, a $C_2$-$C_6$ recycle olefin stream or a $C_3$-$C_4$ bottoms stream from an overhead separation unit may be returned to the metathesis reactor. In one embodiment, as shown in FIG. 1, a light weight olefin stream 44 from an olefin separation unit 40 may be returned to the metathesis reactor 20. In another embodiment, the $C_3$-$C_4$ bottoms stream and the light weight olefin stream 44 are combined together and returned to the metathesis reactor 20. In another embodiment, a $C_{15+}$ bottoms stream 46 from the olefin separation unit 40 is returned to the metathesis reactor 20. In another embodiment, all of the aforementioned recycle streams are returned to the metathesis reactor 20.

In other embodiments, various ester streams downstream of the transesterification unit (discussed below) may also be recycled or returned to the metathesis reactor 20. In certain embodiments, a glycerolysis reaction may be conducted on the recycled ester stream to prevent or limit the amount of free glycerol entering the metathesis reactor 20. In some embodiments, the recycled ester stream will undergo a purification step to limit the amount of methanol being recycled to the metathesis reactor 20. In some embodiments, the recycled ester stream is combined with the low-molecular-weight olefin 14 and/or mid-weight olefin 15 prior to conducting the glycerolysis reaction and entering the metathesis reactor 20. The glycerolysis reaction may also limit or prevent free fatty acid methyl esters from entering the metathesis reaction and subsequently exiting the metathesis reactor as free fatty acid methyl esters that may boil close to various high-valued olefin products. In such cases, these methyl ester components may be separated with the olefins during the separation of the olefins and esters. Such methyl ester components may be difficult to separate from the olefins by distillation.

The metathesis reaction in the metathesis reactor 20 produces a metathesized product 22. In one embodiment, the metathesized product 22 enters a flash vessel operated under temperature and pressure conditions which target $C_2$ or $C_2$-$C_3$ compounds to flash off and be removed overhead. The $C_2$ or $C_2$-$C_3$ light ends are comprised of a majority of hydrocarbon compounds having a carbon number of 2 or 3. In certain embodiments, the $C_2$ or $C_2$-$C_3$ light ends are then sent to an overhead separation unit, wherein the $C_2$ or $C_2$-$C_3$ compounds are further separated overhead from the heavier compounds that flashed off with the $C_2$-$C_3$ compounds. These heavier compounds are typically $C_3$-$C_5$ compounds carried overhead with the $C_2$ or $C_2$-$C_3$ compounds. After separation in the overhead separation unit, the overhead $C_2$ or $C_2$-$C_3$ stream may then be used as a fuel source. These hydrocarbons have their own value outside the scope of a fuel composition, and may be used or separated at this stage for other valued compositions and applications. In certain embodiments, the bottoms stream from the overhead separation unit containing mostly $C_3$-$C_5$ compounds is returned as a recycle stream to the metathesis reactor. In the flash vessel, the metathesized product 22 that does not flash overhead is sent downstream for separation in a separation unit 30, such as a distillation column.

Prior to the separation unit 30, in certain embodiments, the metathesized product 22 may be contacted with a reactant or reagent to deactivate or to extract the catalyst. In certain embodiments, the metathesized product 22 is introduced to an adsorbent or complexing agent to facilitate the separation of the metathesized product 22 from the metathesis catalyst. In one embodiment, the adsorbent or complexing agent is a clay bed. The clay bed will adsorb the metathesis catalyst, and after a filtration step, the metathesized product 22 can be sent to the separation unit 30 for further processing. In another embodiment, the adsorbent or complexing agent is a water soluble phosphine reagent such as tris hydroxymethyl phosphine (THMP). Catalyst may be separated with a water soluble phosphine through known liquid-liquid extraction mechanisms by decanting the aqueous phase from the organic phase.

In some embodiments, the metathesized product 22 may be sent to a catalyst kill drum where the reagent (e.g., THMP aqueous solution) is added to deactivate the metathesis catalyst. THMP may be added at a rate equivalent to at least 1:1, 5:1, 10:1, 25:1, or 50:1 molar ratio relative to the catalyst pumped into the catalyst kill drum.

In certain embodiments, the reagent (e.g., THMP) can be left in the metathesized product 22 and carried along, either in whole or in part, into a subsequent chemical reaction or processing step. In other embodiments, the reagent can be separated and removed from the mixture, either partially or completely, prior to any subsequent reaction or processing step. In some embodiments, passivation and extraction can be coupled into one step (e.g., by providing the reagent in the extracting material).

In one embodiment, the catalyst separation occurs by sending the effluent from the catalyst kill drum to a catalyst decanter drum. The decanter drum may function as a horizontal vessel with a vertical baffle and a boot to collect the water phase containing the metathesis catalyst. In some embodiments, the decanter drum operates at a temperature between approximately 60-90° C. and a pressure between 1-1.5 atm, or approximately 53° C. (127° F.) and 1.1 atm (16 psia).

In other embodiments, the catalyst separation comprises washing or extracting the mixture with a polar solvent (e.g., particularly, though not exclusively, for embodiments in which the reagent is at least partially soluble in the polar solvent). In some embodiments, the polar solvent is added in a subsequent step following catalyst deactivation. In other embodiments, the polar solvent (e.g., water) is added to the metathesized product 22 at approximately the same time as the deactivation reagent (e.g., THMP). Near simultaneous addition of the deactivation reagent and polar solvent to the metathesized product can eliminate the need for an additional reaction/separation vessel, which may simply the process and potentially save capital.

In some embodiments, the polar solvent is at least partially non-miscible with the mixture, such that a separation of layers can occur. In some embodiments, at least a portion of the reagent is partitioned into the polar solvent layer, which can then be separated from the non-miscible remaining layer and removed. Representative polar solvents for use in accordance with the present teachings include but are not limited to water, alcohols (e.g., methanol, ethanol, etc.), ethylene glycol, glycerol, DMF, multifunctional polar compounds including but not limited to polyethylene glycols and/or glymes, ionic liquids, and the like, and combinations thereof. In some embodiments, the mixture is extracted with water. In some embodiments, when a phosphite ester that is at least partially hydrolyzable (e.g., in some embodiments, a phosphite ester having a low molecular weight, including but not limited to trimethyl phosphite, triethyl phosphite, and a combination thereof) is used as a reagent, washing the mixture with water may convert the phosphite ester into a corresponding acid. While neither desiring to be bound by any particular theory nor intending to limit in any measure the scope of the appended claims or their equivalents, it is presently believed that such a hydrolysis may occur more rapidly with lower molecular weight esters.

In some embodiments, when extraction with a polar solvent is desired, the extracting may comprise high shear mixing (e.g., mixing of a type sufficient to disperse and/or transport at least a portion of a first phase and/or chemical species into a second phase with which the first phase and/or a chemical species would normally be at least partly immiscible) although such mixing, in some embodiments, may contribute to undesirable emulsion formation. In some embodiments, the extracting comprises low-intensity mixing (e.g., stirring that is not high shear). The present teachings are in no way restricted to any particular type or duration of mixing. However, for purposes of illustration, in some embodiments, the extracting comprises mixing the polar solvent and the mixture together for at least about 1 second, 10 seconds, 30 seconds, 1 minute, 2 minutes, 5 minutes, 10 minutes, 15 minutes, 20 minutes, 25 minutes, 30 minutes, 35 minutes, 40 minutes, 45 minutes, 50 minutes, 55 minutes, or 60 minutes. While neither desiring to be bound by any particular theory nor intending to limit in any measure the scope of the appended claims or their equivalents, it is presently believed that shorter mixing times (e.g., on the order of a second or seconds) are achievable when inline shear mixing is used for mixing.

When extraction with a polar solvent is desired, the present teachings are in no way restricted to any particular amount of polar solvent added to the mixture for the extracting. However, for purposes of illustration, in some embodiments, the amount by weight of polar solvent (e.g., water) added to the mixture for the extracting is more than the weight of the mixture. In some embodiments, the amount by weight of polar solvent (e.g., water) added to the mixture for the extracting is less than the weight of the mixture. In some embodiments, the weight ratio of the mixture to the water added to the mixture is at least about 1:1, 2:1, 3:1, 4:1, 5:1, 6:1, 7:1, 8:1, 9:1, 10:1, 20:1, 40:1, or 100:1. For higher oil to water ratios, extraction and separation using a centrifuge and/or coalescer may be desirable.

In some embodiments, when extraction with a polar solvent is desired, methods for suppressing dehydrogenation in accordance with the present teachings further comprise allowing a settling period following the polar solvent wash to promote phase separation. The present teachings are in no way restricted to any particular duration of settling period. However, for purposes of illustration, in some embodiments, the settling period is at least about 1 minute, 2 minutes, 5 minutes, 10 minutes, 15 minutes, 30 minutes, 60 minutes, or 120 minutes.

In addition to or as an alternative to washing the mixture with a polar solvent to remove the reagent (e.g., THMP)—a method in accordance with the present teachings can optionally further comprise removing at least a portion of the reagent by adsorbing it onto an adsorbent, which optionally can then be physically separated from the mixture (e.g., via filtration, centrifugation, crystallization, or the like). In some embodiments, the adsorbent is polar. Representative adsorbents for use in accordance with the present teachings include but are not limited to carbon, silica, silica-alumina, alumina, clay, magnesium silicates (e.g., Magnesols), the synthetic silica adsorbent sold under the tradename TRISYL by W. R. Grace & Co., diatomaceous earth, polystyrene, macroporous (MP) resins, and the like, and combinations thereof.

Additionally, in certain embodiments, prior to the separation unit 30 (and after catalyst separation, in some instances), the metathesis product 22 may be sent to a hydrogenation unit, wherein the carbon-carbon double bonds in the olefins and esters are partially to fully saturated with hydrogen gas. Hydrogenation may be conducted according to any known method in the art for hydrogenating double bond-containing compounds such as the olefins and esters present in the metathesis product 22. In certain embodiments, in the hydrogenation unit, hydrogen gas is reacted with the metathesis product 22 in the presence of a hydrogenation catalyst to produce a hydrogenated product comprising partially to fully hydrogenated paraffins/olefins and partially to fully hydrogenated esters.

In some embodiments, the metathesis product 22 is hydrogenated in the presence of a hydrogenation catalyst comprising nickel, copper, palladium, platinum, molybdenum, iron, ruthenium, osmium, rhodium, or iridium, individually or in combinations thereof. Useful catalyst may be heterogeneous or homogeneous. In some embodiments, the catalysts are supported nickel or sponge nickel type catalysts.

In some embodiments, the hydrogenation catalyst comprises nickel that has been chemically reduced with hydrogen to an active state (i.e., reduced nickel) provided on a support. The support may comprise porous silica (e.g., kieselguhr, infusorial, diatomaceous, or siliceous earth) or alumina. The catalysts are characterized by a high nickel surface area per gram of nickel.

Commercial examples of supported nickel hydrogenation catalysts include those available under the trade designations "NYSOFACT", "NYSOSEL", and "NI 5248 D" (from BASF Catalysts LLC, Iselin, N.J.). Additional supported nickel hydrogenation catalysts include those commercially available under the trade designations "PRICAT 9910", "PRICAT 9920", "PRICAT 9908", "PRICAT 9936" (from Johnson Matthey Catalysts, Ward Hill, Mass.).

The supported nickel catalysts may be of the type described in U.S. Pat. No. 3,351,566, U.S. Pat. No. 6,846,772, EP 0168091, and EP 0167201, incorporated by reference herein in their entireties. Hydrogenation may be carried out in a batch or in a continuous process and may be partial hydrogenation or complete hydrogenation. In certain embodiments, the temperature ranges from about 50° C. to about 350° C., about 100° C. to about 300° C., about 150° C. to about 250° C., or about 100° C. to about 150° C. The desired temperature may vary, for example, with hydrogen gas pressure. Typically, a higher gas pressure will require a lower temperature. Hydrogen gas is pumped into the reaction vessel to achieve a desired pressure of $H_2$ gas. In certain embodiments, the $H_2$ gas pressure ranges from about 15 psig (1 atm) to about 3000 psig (204.1 atm), about 15 psig (1 atm) to about 90 psig (6.1 atm), or about 100 psig (6.8 atm) to about 500 psig (34 atm). As the gas pressure increases, more specialized high-pressure processing equipment may be required. In certain embodiments, the reaction conditions are "mild," wherein the temperature is approximately between approximately 50° C. and approximately 100° C. and the $H_2$ gas pressure is less than approximately 100 psig. In other embodiments, the temperature is between about 100° C. and about 150° C., and the pressure is between about 100 psig (6.8 atm) and about 500 psig (34 atm). When the desired degree of hydrogenation is reached, the reaction mass is cooled to the desired filtration temperature.

The amount of hydrogenation catalyst is typically selected in view of a number of factors including, for example, the type of hydrogenation catalyst used, the amount of hydrogenation catalyst used, the degree of unsaturation in the material to be hydrogenated, the desired rate of hydrogenation, the desired degree of hydrogenation (e.g., as measure by iodine value (IV)), the purity of the reagent, and the $H_2$ gas pressure. In some embodiments, the hydrogenation catalyst is used in an amount of about 10 weight % or less, for example, about 5 weight % or less or about 1 weight % or less.

When the desired degree of hydrogenation is reached, the reaction mass is cooled to the desired filtration temperature. During hydrogenation, the carbon-carbon double bonds are partially to fully saturated by the hydrogen gas. In one embodiment, the olefins in the metathesis product 22 are reacted with hydrogen to form a fuel composition comprising only or mostly paraffins. Additionally, the esters from the metathesis product are fully or nearly fully saturated in the hydrogenation unit. In another embodiment, the resulting hydrogenated product includes only partially saturated paraffins/olefins and partially saturated esters.

In the separation unit 30, in certain embodiments, the metathesized product 22 (from a hydrogenation unit, metathesis reactor 20, or catalyst separation unit) is separated into at least two product streams. In one embodiment, the metathesized product 22 is sent to the separation unit 30, or distillation column, to separate the olefins 32 from the esters 34. In another embodiment, a byproduct stream comprising $C_7$'s and cyclohexadienes (e.g., 1,4-cyclohexadiene) may be removed in a side-stream from the separation unit 30. In certain embodiments, the separated olefins 32 may comprise hydrocarbons with carbon numbers up to 24. In certain embodiments, the esters 34 may comprise metathesized glycerides. In other words, the lighter end olefins 32 are preferably separated or distilled overhead for processing into olefin compositions, while the esters 34, comprised mostly of compounds having carboxylic acid/ester functionality, are drawn into a bottoms stream. Based on the quality of the separation, it is possible for some ester compounds to be carried into the overhead olefin stream 32, and it is also possible for some heavier olefin hydrocarbons to be carried into the ester stream 34. Additionally, the separated cyclohexadienes (e.g., 1,4-cyclohexadiene) may be further processed in a dehydrogenation step to form benzene. Examples of catalytic dehydrogenation catalysts include platinum supported on alumina. Examples of oxidative dehydrogenation catalysts include mixed metal oxides consisting of molybdenum, vanadium, niobium, tellurium, magnesium, and/or aluminum. Other dehydrogenation catalysts examples include cerium/zirconium, alkaline earth/nickel, calcium-nickel-phosphate, chromium, iron-chromium oxide, bismuth/molybdenum, tin/antimony, silver, copper.

In one embodiment, the olefins 32 may be collected and sold for any number of known uses. In other embodiments, the olefins 32 are further processed in an olefin separation unit 40 and/or hydrogenation unit 50 (where the olefinic bonds are saturated with hydrogen gas 48, as described below). In other embodiments, esters 34 comprising heavier end glycerides and free fatty acids are separated or distilled as a bottoms product for further processing into various products. In certain embodiments, further processing may target the production of the following non-limiting examples: fatty acid methyl esters; biodiesel; 9DA esters, 9UDA esters, and/or 9DDA esters; 9DA, 9UDA, and/or 9DDA; alkali metal salts and alkaline earth metal salts of 9DA, 9UDA, and/or 9DDA; diacids, and/or diesters of the transesterified products; and mixtures thereof. In certain embodiments, further processing may target the production of $C_{15}$-$C_{18}$ fatty acids and/or esters. In other embodiments, further processing may target the production of diacids and/or diesters. In yet other embodiments, further processing may target the production of compounds having molecular weights greater than the molecular weights of stearic acid and/or linolenic acid.

As shown in FIG. 1, regarding the overhead olefins 32 from the separation unit 30, the olefins 32 may be further separated or distilled in the olefin separation unit 40 to separate the various compositions. The olefin separation unit 40 may comprise a number of distillation towers. In some embodiments, the various composition streams are separated using at least four distillation towers. In other embodiments, three towers or less are used to separate the olefin compositions.

In one embodiment, light end olefins 44 consisting of mainly $C_2$-$C_9$ compounds may be distilled into an overhead stream from the olefin separation unit 40. In certain embodiments, the light end olefins 44 are comprised of a majority of $C_3$-$C_8$ hydrocarbon compounds. In other embodiments, heavier olefins having higher carbon numbers may be separated overhead into the light end olefin stream 44 to assist in targeting a specific fuel composition. The light end olefins 44 may be recycled to the metathesis reactor 20, purged from the system for further processing and sold, or a combination of the two. In one embodiment, the light end olefins 44 may be partially purged from the system and partially recycled to the metathesis reactor 20. With regards to the other streams in the olefin separation unit 40, a heavier $C_{16+}$, $C_{18+}$, $C_{20+}$, $C_{22+}$, or $C_{24+}$ compound stream may be separated out as an olefin bottoms stream 46. This olefin bottoms stream 46 may be purged or recycled to the metathesis reactor 20 for further processing, or a combination of the two. In another embodiment, a center-cut olefin stream 42 may be separated out of the olefin distillation unit for further processing. The center-cut olefins 42 may be designed to target a selected carbon number range for a specific fuel composition. As a non-limiting example, a $C_5$-$C_{15}$ distribution may be targeted for further processing into a naphtha-type jet fuel. Alternatively, a $C_8$-$C_{16}$ distribution may be targeted for further processing into a kerosene-type jet fuel. In another embodiment, a $C_8$-$C_{25}$ distribution may be targeted for further processing into a diesel fuel.

In some embodiments, processing steps may be conducted to maximize alpha olefin purity. In other embodiments, processing steps may be conducted to maximize $C_{10}$ olefin purity. For example, $C_{10+}$ olefins from the separation unit 30 or a particular olefin stream may be reacted with ethylene in the presence of a metathesis catalyst in a secondary metathesis reactor to improve the $C_{10}$ olefin purity. In one embodiment, the metathesis catalyst is a rhenium oxide catalyst (e.g., rhenium oxide supported on alumina). In another embodiment, the metathesis is a tungsten oxide catalyst (e.g., tungsten oxide supported on silica). This metathesis reaction may be conducted in a fixed bed reactor. In some embodiments, the ethylene reagent can be recycled back to the secondary metathesis reactor. Lighter olefins ($C_4$-$C_9$) from the secondary metathesis reactor may be mixed with the main metathesis reactor olefins from the separation unit 30 for further processing.

In certain embodiments, the olefins 32 may be oligomerized to form poly-alpha-olefins (PAOs) or poly-internal-olefins (PIOs), mineral oil substitutes, and/or biodiesel fuel. The oligomerization reaction may take place after the distillation unit 30 or after the overhead olefin separation unit 40. In certain embodiments, byproducts from the oligomerization reactions may be recycled back to the metathesis reactor 20 for further processing.

In other embodiments, the olefins 32, light end olefins 44, or center-cut olefins 42 may be self-metathesized in the presence of a metathesis catalyst in a secondary metathesis reactor in order to produce heavier weight $C_{14+}$, $C_{16+}$, or $C_{18+}$ olefin products. In one embodiment, the metathesis catalyst is a rhenium oxide catalyst (e.g., rhenium oxide supported on alumina). In another embodiment, the metathesis is a tungsten oxide catalyst (e.g., tungsten oxide supported on silica). This metathesis reaction may be conducted in a fixed bed reactor. The heavier weight $C_{14+}$, $C_{16+}$, or $C_{18+}$ olefins may be used as surfactants or oil lubes. In some embodiments, the lighter olefin byproducts from the self-metathesis reaction may be recycled back to the secondary metathesis reactor or primary metathesis reactor 20 for further processing.

As mentioned, in one embodiment, the olefins 32 from the separation unit 30 may be sent directly to the hydrogenation unit 50. In another embodiment, the center-cut olefins 42 from the overhead olefin separation unit 40 may be sent to the hydrogenation unit 50. Hydrogenation may be conducted according to any known method in the art for hydrogenating double bond-containing compounds such as the olefins 32 or center-cut olefins 42. In certain embodiments, in the hydrogenation unit 50, hydrogen gas 48 is reacted with the olefins 32 or center-cut olefins 42 in the presence of a hydrogenation catalyst to produce a hydrogenated product 52.

Typical hydrogenation catalysts and reaction conditions are discussed above. During hydrogenation, the carbon-carbon double bond containing compounds in the olefins are partially to fully saturated by the hydrogen gas 48. In one embodiment, the resulting hydrogenated product 52 includes hydrocarbons with a distribution centered between approximately $C_{10}$ and $C_{1-2}$ hydrocarbons for naphtha- and kerosene-type jet fuel compositions. In another embodiment, the distribution is centered between approximately $C_{16}$ and $C_{18}$ for a diesel fuel composition.

In certain embodiments, after hydrogenation, the hydrogenation catalyst may be removed from the hydrogenated product 52 using known techniques in the art, for example, by filtration. In some embodiments, the hydrogenation catalyst is removed using a plate and frame filter such as those commercially available from Sparkler Filters, Inc., Conroe Tex. In some embodiments, the filtration is performed with the assistance of pressure or a vacuum. In order to improve filtering performance, a filter aid may be used. A filter aid may be added to the product directly or it may be applied to the filter. Representative non-limiting examples of filtering aids include diatomaceous earth, silica, alumina, and carbon. Typically, the filtering aid is used in an amount of about 10 weight % or less, for example, about 5 weight % or less or about 1 weight % or less. Other filtering techniques and filtering aids also may be employed to remove the used hydrogenation catalyst. In other embodiments the hydrogenation catalyst is removed using centrifugation followed by decantation of the product.

In certain embodiments, based upon the quality of the hydrogenated product 52 produced in the hydrogenation unit 50, it may be preferable to isomerize the olefin hydrogenated product 52 to assist in targeting of desired fuel properties such as flash point, freeze point, energy density, cetane number, or end point distillation temperature, among other parameters. Isomerization reactions are well-known in the art, as described in U.S. Pat. Nos. 3,150,205; 4,210,771; 5,095,169; and 6,214,764, herein incorporated by reference in their entireties. In one embodiment, the isomerization reaction at this stage may also crack some of the $C_{15+}$ compounds remaining, which may further assist in producing a fuel composition having compounds within the desired carbon number range, such as 5 to 16 for a jet fuel composition.

In certain embodiments, the isomerization may occur concurrently with the hydrogenation step in the hydrogenation unit 50, thereby targeting a desired fuel product. In other embodiments, the isomerization step may occur before the hydrogenation step (i.e., the olefins 32 or center-cut olefins 42 may be isomerized before the hydrogenation unit 50). In yet other embodiments, it is possible that the isomerization step may be avoided or reduced in scope based upon the selection of low-molecular-weight olefin(s) 14 and/or mid-weight olefin(s) 15 used in the metathesis reaction.

In certain embodiments, the hydrogenated product 52 comprises approximately 15-25 weight % $C_7$, approximately <5 weight % $C_8$, approximately 20-40 weight % $C_9$, approximately 20-40 weight % $C_{10}$, approximately <5 weight % approximately 15-25 weight % $C_{12}$, approximately <5 weight % $C_{13}$, approximately <5 weight % $C_{14}$, approximately <5 weight % $C_{15}$, approximately <1 weight % $C_{16}$, approximately <1 weight % $C_{17}$, and approximately <1 weight % $C_{18}$+. In certain embodiments, the hydrogenated product 52 comprises a heat of combustion of at least approximately 40, 41, 42, 43 or 44 MJ/kg (as measured by ASTM D3338). In certain embodiments, the hydrogenated product 52 contains less than approximately 1 mg sulfur per kg hydrogenated product (as measured by ASTM D5453). In other embodiments, the hydrogenated product 52 comprises a density of approximately 0.70-0.75 (as measured by ASTM D4052). In other embodiments, the hydrogenated product has a final boiling point of approximately 220-240° C. (as measured by ASTM D86).

The hydrogenated product 52 produced from the hydrogenation unit 50 may be used as a fuel composition, non-limiting examples of which include jet, kerosene, or diesel fuel. In certain embodiments, the hydrogenated product 52 may contain byproducts from the hydrogenation, isomerization, and/or metathesis reactions. As shown in FIG. 1, the hydrogenated product 52 may be further processed in a fuel composition separation unit 60, removing any remaining byproducts from the hydrogenated product 52, such as hydrogen gas, water, $C_2$-$C_9$ hydrocarbons, or $C_{15}$+ hydrocarbons, thereby producing a targeted fuel composition. The fuel composition separation unit 60 may comprise a number of distillation towers. In some embodiments, the various composition streams are separated using at least four distillation towers. In other embodiments, three towers or less are used to separate the fuel compositions.

In one embodiment, the hydrogenated product 52 may be separated into the desired fuel $C_9$-$C_{15}$ product 64, and a light-ends $C_2$-$C_9$ fraction 62 and/or a $C_{15}$+ heavy-ends fraction 66. Distillation may be used to separate the fractions. Alternatively, in other embodiments, such as for a naphtha- or kerosene-type jet fuel composition, the heavy ends fraction 66 can be separated from the desired fuel product 64 by cooling the hydrogenated product 52 to approximately −40° C., −47° C., or −65° C. and then removing the solid, heavy ends fraction 66 by techniques known in the art such as filtration, decantation, or centrifugation.

With regard to the esters 34 from the distillation unit 30, in certain embodiments, the esters 34 may be entirely withdrawn as an ester product stream 36 and processed further or sold for its own value, as shown in FIG. 1. As a non-limiting example, the esters 34 may comprise various triglycerides that could be used as a lubricant. Based upon the quality of separation between olefins and esters, the esters 34 may comprise some heavier olefin components carried with the triglycerides. In other embodiments, the esters 34 may be further processed in a biorefinery or another chemical or fuel processing unit known in the art, thereby producing various products such as biodiesel or specialty chemicals that have higher value than that of the triglycerides, for example. Alternatively, in certain embodiments, the esters 34 may be partially withdrawn from the system and sold, with the remainder further processed in the biorefinery or another chemical or fuel processing unit known in the art.

In certain embodiments, the ester stream 34 is sent to a transesterification unit 70. Within the transesterification unit 70, the esters 34 are reacted with at least one alcohol 38 in the presence of a transesterification catalyst. In certain embodiments, the alcohol comprises methanol and/or ethanol. In another embodiment, the alcohol 38 comprises glycerol (and the transesterification reaction is a glycerolysis reaction). In one embodiment, the transesterification reaction is conducted at approximately 60-70° C. and approximately 1 atm. In certain embodiments, the transesterification catalyst is a homogeneous sodium methoxide catalyst. Varying amounts of catalyst may be used in the reaction, and, in certain embodiments, the transesterification catalyst is present in the amount of approximately 0.5-1.0 weight % of the esters 34.

In certain embodiments, the transesterification reaction may produce a transesterified product 72 comprising monomer terminal olefin esters having the following structure:

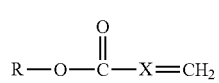

where X is a $C_3$-$C_{18}$ saturated or unsaturated alkyl chain, and R is an alkyl group. In some embodiments, R is methyl.

The transesterification reaction may produce transesterified products 72 including saturated and/or unsaturated monomer fatty acid methyl esters ("FAME"), glycerin, methanol, and/or free fatty acids. In certain embodiments, the transesterified products 72, or a fraction thereof, may comprise a source for biodiesel. In certain embodiments, the transesterified products 72 comprise $C_{10}$-$C_{15}$ or $C_{11}$-$C_{14}$ esters. In certain embodiments, the transesterified products 72 comprise 9DA esters, 9UDA esters, and/or 9DDA esters. Non-limiting examples of 9DA esters, 9UDA esters and 9DDA esters include methyl 9-decenoate ("9-DAME"), methyl 9-undecenoate ("9-UDAME"), and methyl 9-dodecenoate ("9-DDAME"), respectively. As a non-limiting example, in a transesterification reaction, a 9DA moiety of a metathesized glyceride is removed from the glycerol backbone to form a 9DA ester.

As discussed above, the types of transesterified products formed are based upon the reactants entering the metathesis reactor 20. In one particular embodiment, $C_{12}$ methyl esters (9-DDAME) are produced downstream of the metathesis reaction between 3-hexene and a natural oil.

In another embodiment, a glycerin alcohol may be used in the reaction with a glyceride stream. This reaction may produce monoglycerides and/or diglycerides.

In certain embodiments, the transesterified products 72 from the transesterification unit 70 can be sent to a liquid-liquid separation unit, wherein the transesterified products 72 (i.e., FAME, free fatty acids, and/or alcohols) are separated from glycerin. Additionally, in certain embodiments, the glycerin byproduct stream may be further processed in a secondary separation unit, wherein the glycerin is removed and any remaining alcohols are recycled back to the transesterification unit 70 for further processing.

In one embodiment, the transesterified products 72 are further processed in a water-washing unit. In this unit, the transesterified products undergo a liquid-liquid extraction when washed with water. Excess alcohol, water, and glycerin are removed from the transesterified products 72. In another embodiment, the water-washing step is followed by a drying unit in which excess water is further removed from the desired mixture of esters (i.e., specialty chemicals). Such specialty chemicals include non-limiting examples such as 9DA, 9UDA, and/or 9DDA, alkali metal salts and alkaline earth metal salts of the preceding, individually or in combinations thereof.

In one embodiment, the monomer specialty chemical (e.g., 9DA) may be further processed in an oligomerization reaction to form a lactone, which may serve as a precursor to a surfactant.

In certain embodiments, the transesterified products 72 from the transesterification unit 70 or specialty chemicals from the water-washing unit or drying unit are sent to an ester distillation column 80 for further separation of various individual or groups of compounds, as shown in FIG. 1. This separation may include, but is not limited to, the separation of 9DA esters, 9UDA esters, and/or 9DDA esters. In one embodiment, the 9DA ester 82 may be distilled or individually separated from the remaining mixture 84 of transesterified products or specialty chemicals. In certain process conditions, the 9DA ester 82 should be the lightest component in the transesterified product or specialty chemical stream, and come out at the top of the ester distillation column 80. In another embodiment, the remaining mixture 84, or heavier components, of the transesterified products or specialty chemicals may be separated off the bottom end of the column. In certain embodiments, this bottoms stream 84 may potentially be sold as biodiesel.

The 9DA esters, 9UDA esters, and/or 9DDA esters may be further processed after the distillation step in the ester distillation column. In one embodiment, under known operating conditions, the 9DA ester, 9UDA ester, and/or 9DDA ester may then undergo a hydrolysis reaction with water to form 9DA, 9UDA, and/or 9DDA, alkali metal salts and alkaline earth metal salts of the preceding, individually or in combinations thereof.

In certain embodiments, the monomer fatty acid esters from the transesterified products 72 may be reacted with each other to form other specialty chemicals such as dimers.

In other embodiments, specific ester products, such as 9DDA methyl ester, may be enriched through subsequent processing and reaction steps of the transesterified products. In one embodiment, a $C_{10}$ methyl ester stream may be separated from heavier $C_{12+}$ methyl esters. The $C_{10}$ methyl ester stream may then be reacted with 1-butene in the presence of a metathesis catalyst to form $C_{12}$ methyl esters and ethylene. The ethylene may be separated from the methyl esters and the C10 and C12 methyl esters may be removed or returned to an ester distillation column for further processing.

In certain embodiments, the monomer fatty acids and/or monomer fatty acid esters from the transesterified products 72 are isomerized to form isomerized monomer fatty acids and/or isomerized monomer fatty acid esters. The isomerization of the fatty acids and/or fatty acid esters from the transesterified products 72 may be conducted at an elevated temperature (i.e., greater than 25° C.). In certain embodiments, the temperature of the heat treatment for the isomerization reaction is greater than 100° C., greater than 150° C., or greater than 200° C. In other embodiments, the temperature is between 100° C.-300° C., between 150-250° C., or about 200° C. In some embodiments, the heat treatment step is conducted in the presence of an isomerization catalyst. In one particular embodiment, the isomerization catalyst is $(PCy_3)_2$ $(Cl)(H)Ru(CO)$, where "Cy" represents a cyclohexyl group.

In certain embodiments, the monomer fatty acids and/or monomer fatty acid esters that undergo the isomerization reaction are selected from the group consisting of: 9DA, 9DA esters, 9UDA, 9UDA esters, 9DDA, and 9DDA esters. The isomerization of the fatty acids and/or fatty acid esters may produce isomerized monomer fatty acids and/or isomerized monomer fatty acid esters selected from the group consisting of isomerized 9DA, isomerized 9DA esters, isomerized 9UDA, isomerized 9UDA esters, isomerized 9DDA, and isomerized 9DDA esters.

Isomerizing the monomer fatty acids and/or monomer fatty acid esters may improve various performance properties. For example, the isomerized product composition may have an observed broadening of the freezing and melting points, which may allow for transportation of the isomerized fatty acid/ester product composition at higher concentrations of the monomer fatty acids and/or monomer fatty acid esters without incurring shipping problems.

Isomerized monomer fatty acids and/or isomerized monomer fatty acid esters may be used in a variety of different commercial applications, including, but not limited to: lubricants, waxes, films, paints, paint strippers, coatings, plasticizers, resins, binders, solvents, polyols, soil stabilization, chemical grouting, oilfield drilling fluids, crop protection products, surfactants, intermediates, and adhesives.

In certain embodiments, the transesterified product 72 comprises terminal olefin esters and is cross-metathesized with an internal olefin in the presence of a metathesis catalyst to produce a dibasic acid and/or dibasic ester, as well as an olefin byproduct. As mentioned above, the transesterified product 72 may comprise terminal olefins having the following structure:

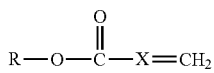

where X is a $C_3$-$C_{18}$ saturated or unsaturated alkyl chain, and R is an alkyl group or hydrogen.

In certain embodiments, the terminal olefin-internal olefin cross-metathesis reaction is conducted at a weight ratio between 1:99 (terminal to internal) and 99:1 (terminal to internal). In other embodiments, the weight ratio of the terminal and internal olefin is between 1:5 and 5:1. In yet other embodiments, the weight ratio between the terminal and internal olefin is between 1:2 and 2:1. In one particular embodiment, the weight ratio between the terminal and internal olefin is approximately 1:1.

In certain embodiments, the terminal olefin is selected from the group consisting of: 4-pentenoic acid ester, 5-hexenoic acid ester, 6-heptenoic acid ester, 7-octenoic acid ester, 8-nonenoic acid ester, 9-decenoic acid ester, 10-undecenoic acid ester, 11-dodecenoic acid ester, 12-tridecenoic acid ester, 13-tetradecenoic acid ester, 14-pentadecenoic acid ester, 15-hexadecenoic acid ester, 16-heptadecenoic acid ester, 17-octadecenoic acid ester, acids thereof, and mixtures thereof. In one particular embodiment, the terminal olefin is 9-decenoic acid ester.

In certain embodiments, the terminal olefin is cross-metathesized with an internal olefin selected from the group consisting of: pentenoic acid esters, hexenoic acid esters, heptenoic acid esters, octenoic acid esters, nonenoic acid esters, decenoic acid esters, undecenoic acid esters, dodecenoic acid esters, tridecenoic acid esters, tetradecenoic acid esters, pentadecenoic acid esters, hexadecenoic acid esters, heptadecenoic acid esters, octadecenoic acid esters, acids thereof, and mixtures thereof. In one particular embodiment, the internal olefin is 9-undecenoic acid ester. In another particular embodiment, the internal olefin is 9-dodecenoic acid ester.

In some embodiments, the internal olefin is formed by reacting a portion of the terminal olefin ester derived from the transesterified product 72 with a low-molecular-weight internal olefin or mid-weight internal olefin in the presence of a metathesis catalyst. In certain embodiments, the low-molecular-weight internal olefin is selected from the group consisting of: 2-butene, 2-pentene, 2-hexene, 3-hexene, 2-heptene, 3-heptene, 2-octene, 3-octene, 4-octene, 2-nonene, 3-nonene, 4-nonene, and mixtures thereof. In one particular embodiment, the low-molecular-weight internal olefin is 2-butene. In another particular embodiment, the low-molecular-weight internal olefin is 3-hexene.

In certain embodiments, at least 70 wt %, 80 wt %, or 90 wt % dibasic ester and/or dibasic acid is formed from the cross-metathesis reaction of a terminal olefin and an internal olefin in the presence of less than 150 ppm, 100 ppm, 50 ppm, 25 ppm, or 10 ppm catalyst. A comparable self-metathesis reaction with terminal olefins (such as 9-decenoic acid ester) under similar reaction conditions may require more catalyst (e.g., more than 150 ppm, or more than 500 ppm) to achieve similar yields of dibasic esters and/or dibasic acids (potentially due to the formation of the ethylene byproduct).

In certain embodiments, the dibasic ester and/or dibasic acid yield is improved by separating the olefin byproduct formed in the cross-metathesis reaction from the metathesis product while the reaction between the terminal olefin and internal olefin is ongoing. In other embodiments, the dibasic ester and/or dibasic acid yield is improved by sparging the metathesis products in the metathesis reactor with a chemically inert gas (e.g., nitrogen, argon, or helium) to ventilate dissolved gases/byproducts (e.g., olefin byproducts) in the metathesis product.

In certain embodiments, the cross-metathesis reaction of the terminal olefin and internal olefin produces a dibasic ester comprising the following structure:

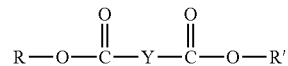

wherein R and R' are independently alkyl or aryl groups, and Y is an olefin comprising between 6 and 36 carbon atoms. In some embodiments, the cross-metathesis reaction forms a $C_{21}$-$C_{24}$ dibasic ester. In one embodiment, the cross-metathesis reaction forms a dibasic ester, where R and R' are methyl and Y is 8-hexadecene (i.e., the dibasic ester formed from the cross-metathesis reaction of a terminal olefin and an internal olefin is dimethyl 9-octadecenedioate).

In some embodiments, the dibasic ester derived from the transesterified product 72 may further undergo a hydrolysis reaction with water to form a dibasic acid having the following structure:

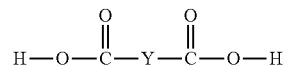

wherein Y is an olefin comprising between 6 and 36 carbon atoms. In one embodiment, Y is 8-hexadecene (i.e., the dibasic acid is 9-octadecene dioic acid).

Following hydrolysis, in some embodiments, the product stream may be sent to a flash column or decanter to remove methanol and water from the diacid.

In other embodiments, the dibasic acid and/or dibasic ester is isomerized to form an isomerized dibasic acid and/or isomerized dibasic ester. The isomerization of the dibasic acid and/or dibasic ester may be conducted at an elevated temperature (i.e., greater than 25° C.). In certain embodiments, the temperature of the heat treatment for the isomerization reaction is greater than 100° C., greater than 150° C., or greater than 200° C. In other embodiments, the temperature is between 100° C.-300° C., between 150-250° C., or about 200° C. In some embodiments, the heat treatment step is conducted in the presence of an isomerization catalyst. In one particular embodiment, the isomerization catalyst is $(PCy_3)_2(Cl)(H)Ru(CO)$, where "Cy" represents a cyclohexyl group.

In certain embodiments, the isomerized dibasic acid and/or isomerized dibasic ester comprises compounds selected from the group consisting of: isomerized dimethyl 9-octadecenedioate or isomerized 9-octadecene dioic acid.

In certain embodiments, the isomerized dibasic acid and/or isomerized dibasic ester is self-metathesized or cross-metathesized with a low-molecular-weight olefin or mid-weight olefin. Typical metathesis reaction conditions and catalysts are discussed in greater detail below. In one embodiment, the isomerized dibasic acid and/or isomerized dibasic ester is self-metathesized in the presence of approximately 10 ppm, 20 ppm, 40 ppm, 50 ppm, 80 ppm, 100 ppm, 120 ppm, or greater than 150 ppm metathesis catalyst.

In certain embodiments, the isomerized fatty acid, isomerized fatty acid ester, dibasic acid, dibasic ester, isomerized dibasic acid, and/or isomerized dibasic ester is hydrogenated.

Typical hydrogenation reaction conditions and catalysts are discussed above. In one particular example, the hydrogenation reaction is conducted in the presence of a nickel based catalyst at approximately 150° C. and 150 psig.

As noted, the self-metathesis of the natural oil, cross-metathesis between the natural oil and low-molecular-weight olefin or mid-weight olefin, or cross-metathesis between a terminal olefin and internal olefin occurs in the presence of a metathesis catalyst. As stated previously, the term "metathesis catalyst" includes any catalyst or catalyst system that catalyzes a metathesis reaction. Any known or future-developed metathesis catalyst may be used, individually or in combination with one or more additional catalysts. Non-limiting exemplary metathesis catalysts and process conditions are described in PCT/US2008/009635, pp. 18-47, incorporated by reference herein. A number of the metathesis catalysts as shown are manufactured by Materia, Inc. (Pasadena, Calif.).

The metathesis process can be conducted under any conditions adequate to produce the desired metathesis products. For example, stoichiometry, atmosphere, solvent, temperature, and pressure can be selected by one skilled in the art to produce a desired product and to minimize undesirable byproducts. The metathesis process may be conducted under an inert atmosphere. Similarly, if a reagent is supplied as a gas, an inert gaseous diluent can be used. The inert atmosphere or inert gaseous diluent typically is an inert gas, meaning that the gas does not interact with the metathesis catalyst to substantially impede catalysis. For example, particular inert gases are selected from the group consisting of helium, neon, argon, nitrogen, individually or in combinations thereof.

In certain embodiments, the metathesis catalyst is dissolved in a solvent prior to conducting the metathesis reaction. In certain embodiments, the solvent chosen may be selected to be substantially inert with respect to the metathesis catalyst. For example, substantially inert solvents include, without limitation, aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc. In one particular embodiment, the solvent comprises toluene.

In other embodiments, the metathesis catalyst is not dissolved in a solvent prior to conducting the metathesis reaction. The catalyst, instead, may be slurried with the natural oil 12, where the natural oil 12 is in a liquid state. Under these conditions, it is possible to eliminate the solvent (e.g., toluene) from the process and eliminate downstream olefin losses when separating the solvent. In other embodiments, the metathesis catalyst may be added in solid state form (and not slurried) to the natural oil 12 (e.g., as an auger feed).

The metathesis reaction temperature may be a rate-controlling variable where the temperature is selected to provide a desired product at an acceptable rate. In certain embodiments, the metathesis reaction temperature is greater than about −40° C., greater than about −20° C., greater than about 0° C., or greater than about 10° C. In certain embodiments, the metathesis reaction temperature is less than about 150° C., or less than about 120° C. In one embodiment, the metathesis reaction temperature is between about 10° C. and about 120° C.

The metathesis reaction can be run under any desired pressure. Typically, it will be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than about 0.1 atm (10 kPa), in some embodiments greater than about 0.3 atm (30 kPa), or greater than about 1 atm (100 kPa). Typically, the reaction pressure is no more than about 70 atm (7000 kPa), in some embodiments no more than about 30 atm (3000 kPa). A non-limiting exemplary pressure range for the metathesis reaction is from about 1 atm (100 kPa) to about 30 atm (3000 kPa).

While the invention as described may have modifications and alternative forms, various embodiments thereof have been described in detail. It should be understood, however, that the description herein of these various embodiments is not intended to limit the invention, but on the contrary, the intention is to cover all modifications, equivalents, and alternatives falling within the spirit and scope of the invention as defined by the claims. Further, while the invention will also be described with reference to the following non-limiting examples, it will be understood, of course, that the invention is not limited thereto since modifications may be made by those skilled in the art, particularly in light of the foregoing teachings.

EXAMPLES

Example 1

A clean, dry, stainless steel jacketed 5-gal. Parr reactor vessel equipped with a dip tube, overhead stirrer, internal cooling/heated coils, temperature probe, sampling valve, and headspace gas release valve was purged with argon to 15 psig. Soybean oil (SBO, 2.5 kg, 2.9 mol, Costco, MWn=864.4 g/mol, 85 weight % unsaturation as determined by gas chromatographic analysis ("by gc"), 1 hour argon sparged in 5-gal container) was added into the Parr reactor. The Parr reactor was sealed and the SBO was purged with argon for 2 hours while cooling to 10° C. After 2 hours, the reactor was vented until the internal pressure reached 10 psig. The dip tube valve on the reactor was connected to a 1-butene cylinder (Airgas, CP grade, 33 psig headspace pressure, >99 weight %) and re-pressurized to 15 psig of 1-butene. The reactor was vented again to 10 psig to remove residual argon in the headspace. The SBO was stirred at 350 rpm and 9-15° C. under 18-28 psig 1-butene until 3 mol 1-butene per SBO olefin bond was transferred into the reactor (approximately 2.2 kg 1-butene over approximately 4-5 hours). A toluene solution of [1,3-Bis-(2,4,6-trimethylphenyl)-2-imidazolidinylidene]dichlororuthenium(3-methyl-2-butenylidene)(tricyclohexylphosphine) (C827, Materia) was prepared in Fischer-Porter pressure vessel by dissolving 130 mg catalyst in 30 grams of toluene as a catalyst carrier (10 mol ppm per olefin bond of SBO) and was added to the reactor via the reactor dip tube by pressurizing the headspace inside the Fischer-Porter vessel to 50-60 psig with argon. The Fischer-Porter vessel and dip tube were rinsed with an additional 30 g toluene. The reaction mixture was stirred for 2.0 hours at 60° C. The reaction mixture was allowed to cool to ambient temperature while the gases in the headspace were vented. After the pressure was released, the reaction mixture was transferred to a 3-neck round bottom flask containing 58 g bleaching clay (2% w/w SBO, Pure Flow B80 CG) and a magnetic stir bar. The reaction mixture was treated by stirring at 85° C. under argon. After 2 hours, during which time any remaining 1-butene was allowed to vent, the reaction mixture was allowed to cool to 40° C. and filtered through a fritted glass filter. An aliquot of the product mixture was found by gas chromatographic analysis (following transesterification with 1% w/w NaOMe in methanol at 60° C.) to contain approximately 22 weight % methyl 9-decenoate, approximately 16 weight % methyl 9-dodecenoate, approximately 3 weight % dimethyl 9-octadecenedioate, and approximately 3 weight % methyl 9-octadecenoate (by gc). These results compare favorably with the calculated yields at equilibrium of 23.4 wt % methyl 9-decenoate, 17.9 wt % methyl 9-dodecenoate, 3.7 wt % dimethyl 9-octadecenedioate, and 1.8 wt % methyl 9-octadecenoate.

Example 2

By the general procedures described in example 1, a reaction was performed using 1.73 kg SBO and 3 mol 1-butene/SBO double bond. An aliquot of the product mixture was found by gas chromatographic analysis following transesterification with 1% w/w NaOMe in methanol at 60° C. to contain approximately 24 weight % methyl 9-decenoate, approximately 18 weight % methyl 9-dodecenoate, approximately 2 weight % dimethyl 9-octadecenedioate, and approximately 2 weight % methyl 9-octadecenoate (as determined by gc).

Example 3

By the general procedures described in example 1, a reaction was performed using 1.75 kg SBO and 3 mol 1-butene/SBO double bond. An aliquot of the product mixture was found by gas chromatographic analysis following transesterification with 1% w/w NaOMe in methanol at 60° C. to contain approximately 24 weight % methyl 9-decenoate, approximately 17 weight % methyl 9-dodecenoate, approximately 3 weight % dimethyl 9-octadecenedioate, and approximately 2 weight % methyl 9-octadecenoate (as determined by gc).

Example 4

By the general procedures described in example 1, a reaction was performed using 2.2 kg SBO, 3 mol 1-butene/SBO double bond, and the 60 g of toluene used to transfer the catalyst was replaced with SBO. An aliquot of the product mixture was found by gas chromatographic analysis following transesterification with 1% w/w NaOMe in methanol at 60° C. to contain approximately 25 weight % methyl 9-decenoate, approximately 18 weight % methyl 9-dodecenoate, approximately 3 weight % dimethyl 9-octadecenedioate, and approximately 1 weight % methyl 9-octadecenoate (as determined by gc).

Example 5

A 12-liter, 3-neck, glass round bottom flask that was equipped with a magnetic stir bar, heating mantle, and temperature controller was charged with 8.42 kg of the combined reaction products from examples 1-4. A cooling condenser with a vacuum inlet was attached to the middle neck of the flask and a receiving flask was connected to the condenser. Hydrocarbon olefins were removed from the reaction product by vacuum distillation over the follow range of conditions: 22-130° C. pot temperature, 19-70° C. distillation head temperature, and 2000-160 μtorr pressure. The weight of material remaining after the volatile hydrocarbons were removed was 5.34 kg. An aliquot of the non-volatile product mixture was found by gas chromatographic analysis following transesterification with 1% w/w NaOMe in methanol at 60° C. to contain approximately 32 weight % methyl 9-decenoate, approximately 23 weight % methyl 9-dodecenoate, approximately 4 weight % dimethyl 9-octadecenedioate, and approximately 5 weight % methyl 9-octadecenoate (as determined by gc).

Example 6

A 12-liter, 3-neck round bottom flask that was fitted with a magnetic stir bar, condenser, heating mantle, temperature probe, and gas adapter was charged with 4 liters of 1% w/w NaOMe in MeOH and 5.34 kg of the non-volatile product mixture produced in example 5. The resulting light yellow heterogeneous mixture was stirred at 60° C. After about an hour, the mixture turned a homogeneous orange color (detected pH=11.) After a total reaction time of 2 hours, the mixture was cooled to ambient temperature and two layers were observed. The organic phase was washed twice with 3 L of 50% (v/v) aqueous MeOH, separated, and neutralized by washing with glacial HOAc in MeOH (1 mol HOAc/mol NaOMe) to a detected pH of 6.5, yielding 5.03 kg.

Example 7

A glass, 12 L, 3-neck round bottom flask fitted with a magnetic stirrer, packed column, and temperature controller was charged with the methyl ester mixture (5.03 kg) produced in example 6 and placed in the heating mantle. The column attached to the flask was a 2-inch×36-inch glass column containing 0.16" Pro-Pak™ stainless steel saddles. The distillation column was attached to a fractional distillation head to which a 1 L pre-weighed round bottom flask was fitted for collecting the distillation fractions. The distillation was carried out under vacuum at 100-120 μtorr. A reflux ratio of 1:3 was used for isolating both methyl 9-decenoate (9-DAME) and methyl 9-dodecenoate (9-DDAME). A reflux ratio of 1:3 referred to 1 drop collected for every 3 drops sent back to the distillation column. The samples collected during the distillation, the vacuum distillation conditions, and the 9-DAME and 9-DDAME content of the fractions, as determined by gc, are shown in Table 1. Combining fractions 2-7 yielded 1.46 kg methyl 9-decenoate with 99.7% purity. After collecting fraction 16, 2.50 kg of material remained in the distillation pot: it was found by gc to contain approximately 14 weight % 9-DDAME, approximately 42 weight % methyl palmitate, and approximately 12 weight % methyl stearate.

TABLE 1

| Distillation Fractions # | Head temp. (° C.) | Pot temp. (° C.) | Vacuum (μtorr) | Weight (g) | 9-DAME (wt %) | 9-DDAME (wt %) |
|---|---|---|---|---|---|---|
| 1 | 40-47 | 104-106 | 110 | 6.8 | 80 | 0 |
| 2 | 45-46 | 106 | 110 | 32.4 | 99 | 0 |
| 3 | 47-48 | 105-110 | 120 | 223.6 | 99 | 0 |
| 4 | 49-50 | 110-112 | 120 | 283 | 99 | 0 |
| 5 | 50 | 106 | 110 | 555 | 99 | 0 |
| 6 | 50 | 108 | 110 | 264 | 99 | 0 |
| 7 | 50 | 112 | 110 | 171 | 99 | 0 |
| 8 | 51 | 114 | 110 | 76 | 97 | 1 |
| 9 | 65-70 | 126-128 | 110 | 87 | 47 | 23 |
| 10 | 74 | 130-131 | 110 | 64 | 0 | 75 |
| 11 | 75 | 133 | 110 | 52.3 | 0 | 74 |
| 12 | 76 | 135-136 | 110 | 38 | 0 | 79 |
| 13 | 76 | 136-138 | 100 | 52.4 | 0 | 90 |
| 14 | 76 | 138-139 | 100 | 25.5 | 0 | 85 |
| 15 | 76-77 | 140 | 110 | 123 | 0 | 98 |
| 16 | 78 | 140 | 100 | 426 | 0 | 100 |

Example 8

A reaction was performed by the general procedures described in example 1 with the following changes: 2.2 kg SBO, 7 mol propene/mol SBO double bond, and 200 mg [1,3-Bis-(2,4,6-trimethylphenyl)-2-imidazolidinylidene]

dichlororuthenium(benzylidene)(tricyclohexyl-phosphine) [C848 catalyst, Materia Inc., Pasadena, Calif., USA, 90 ppm (w/w) vs. SBO] at a reaction temperature of 40° C. were used. The catalyst removal step using bleaching clay also was replaced by the following: after venting excess propene, the reaction mixture was transferred into a 3-neck round bottom flask to which 50 mol of tris(hydroxymethyl)phosphine (THMP)/mol C848 catalyst was added. The THMP was formed as a 1.0 M solution in isopropanol, where phosphonium salt, inorganic salt, formaldehyde, THMPO, and THMP were mixed together. The resulting hazy yellow mixture was stirred for 20 hours at 60° C., transferred to a 6-L separatory funnel and extracted with 2×2.5 L deionized $H_2O$. The organic layer was separated and dried over anhydrous $Na_2SO_4$ for 4 hours, then filtered through a fritted glass filter containing a bed of silica gel.

Example 9

A reaction was performed by the general procedures described in example 8, except that 3.6 kg SBO and 320 mg C848 catalyst were used. Following catalyst removal, the reaction product from example 9 was combined with that from example 8, yielding 5.12 kg of material. An aliquot of the combined product mixture was found by gas chromatographic analysis following transesterification with 1% w/w NaOMe in methanol at 60° C. to contain approximately 34 weight % methyl 9-decenoate, approximately 13 weight % methyl 9-undecenoate, <1 weight % dimethyl 9-octadecenedioate, and <1 weight % methyl 9-octadecenoate (as determined by gc).

Hydrocarbon olefins were removed from the 5.12 kg of combined reaction product described above by vacuum distillation by the general procedure described in example 5. The weight of material remaining after the volatile olefins were removed was 4.0 kg. An aliquot of the non-volatile product mixture was found by gas chromatographic analysis following transesterification with 1% w/w NaOMe in methanol at 60° C. to contain approximately 46 weight % methyl 9-decenoate, approximately 18 weight % methyl 9-undecenoate, approximately 2 weight % dimethyl 9-octadecenedioate, and approximately 1 weight % methyl 9-octadecenoate (as determined by gc).

Example 10

Two reactions were performed by the general procedures described in example 8, except that for each reaction, 3.1 kg SBO and 280 mg C848 catalyst were used. Following catalyst removal, the reaction products from the two preparations were combined, yielding 5.28 kg of material. An aliquot of the combined product mixture was found by gas chromatographic analysis following transesterification with 1% w/w NaOMe in methanol at 60° C. to contain approximately 40 weight % methyl 9-decenoate, approximately 13 weight % methyl 9-undecenoate, approximately 2 weight % dimethyl 9-octadecenedioate, and approximately 1 weight % methyl 9-octadecenoate (as determined by gc).

Hydrocarbon olefins were removed from the 5.28 kg of combined reaction product by vacuum distillation by the general procedure described in example 5. The weight of material remaining after the volatile olefins were removed was 4.02 kg. An aliquot of the non-volatile product mixture was found by gas chromatographic analysis following transesterification with 1% w/w NaOMe in methanol at 60° C. to contain approximately 49 weight % methyl 9-decenoate, approximately 16 weight % methyl 9-undecenoate, approximately 2 weight % dimethyl 9-octadecenedioate, and approximately 3 weight % methyl 9-octadecenoate (as determined by gc).

Example 11

By the general procedures described in example 10, two metathesis reactions were performed using SBO, 7 mol cis-2-butene/mol SBO double bond, and 220 mg C848 catalyst/kg SBO. Following catalyst removal, the reaction products from the two preparations were combined, yielding 12.2 kg of material. An aliquot of the combined product mixture was found by gas chromatographic analysis following transesterification with 1% w/w NaOMe in methanol at 60° C. to contain approximately 49 weight % methyl 9-undecenoate, approximately 2 weight % dimethyl 9-octadecenedioate, and approximately 1 weight % methyl 9-octadecenoate (as determined by gc).

Hydrocarbon olefins were removed from the 12.2 kg of combined reaction product by vacuum distillation by the general procedure described in example 5. The weight of material remaining after the volatile olefins were removed was 7.0 kg. An aliquot of the non-volatile product mixture was found by gas chromatographic analysis following transesterification with 1% w/w NaOMe in methanol at 60° C. to contain approximately 57 weight % methyl 9-undecenoate, approximately 4 weight % dimethyl 9-octadecenedioate, and approximately 2 weight % methyl 9-octadecenoate (as determined by gc).

Example 12

By the general procedures described in example 1, approximately 7 kg of cross metathesis product was produced by reacting SBO with 3 mol 1-butene/mol SBO double bond using 43 mg C827 catalyst/kg SBO, following catalyst removal with THMP. An initial 2.09 kg portion of the metathesis product was hydrogenated at 136° C. and 400 psig $H_2$ until hydrogen uptake ceased in a one gallon batch autoclave using 105 g of Johnson-Matthey A-7000 Sponge Metal™ catalyst. The resulting mixture was filtered warm (22-55° C.), yielding 1.40 kg filtrate and 350 g of a mixture consisting of the catalyst and the hydrogenated product. The entirety of the catalyst-containing mixture was returned to the one gallon reactor along with a second 2.18 kg portion of the metathesis product and a second hydrogenation reaction was similarly carried out until hydrogen uptake ceased. The catalyst was allowed to settle and the majority of the organic product was decanted and filtered, yielding 1.99 kg filtrate and 380 g catalyst-hydrogenated product mixture. The remaining approximately 3 kg of metathesis product was hydrogenated in two additional batch reactions that in like manner were carried out using the catalyst from the previous reaction, yielding 1.65 kg and 1.28 kg of hydrogenated product, respectively. The total weight of hydrogenated product that was isolated after filtration was 6.32 kg. Aliquots of the hydrogenated product were found by gas chromatographic analysis to contain approximately 30 weight % $C_6$-$C_{18}$ n-paraffins and approximately 70 weight % triglycerides. The relative distribution of the $C_8$-$C_{18}$ n-paraffins contained in the hydrogenated product compares well with the calculated distribution of olefins by carbon number: observed (calculated) 2.3 (0.6) weight % $C_8$, 35.6 (36.2) weight % $C_9$, 30.0 (27.6) weight % $C_{10}$, 0.6 (0.1) weight % $C_{11}$, 22.2 (23.6) weight % $C_{12}$, 3.4 (3.7) weight % $C_{13}$, 0.1 (0.0) weight % $C_{14}$, 4.4 (6.3) weight % $C_{15}$, 0.4 (0.4) weight % $C_{16}$, 0.1 (0.0) weight % $C_{17}$, and 1.0 (1.6) weight % $C_{18}$. The paraffin components were separated by wiped film evaporation from a 4.84 kg aliquot of the hydrogenated paraffin/triglyceride product. An initial wiped film evaporation was carried out at 75° C., 100 torr, 300 rpm, and condensation temperature of 15° C. using a feed rate of 300 g/h and yielded a condensate that was subjected to a second wiped film evaporation at 125° C., 90 torr, 300 rpm, and condensation temperature of 10° C. to remove the lighter alkanes. The resultant residual liquid was found by gas chromatography to contain the following distribution of n-alkanes: 17.5 weight % $C_7$, 1.7 weight % $C_8$, 31.0 weight % $C_9$, 28.3 weight % $C_{10}$, 0.6 weight % $C_{11}$, 17.4 weight % $C_{12}$, 2.1 weight % $C_{13}$, 0.1 weight % $C_{14}$, 1.2 weight % $C_{15}$, 0.1 weight % $C_{18}$, 0.0 weight % $C_{17}$, and 0.1 weight % $C_{18}$. The material was found to have a heat of combustion of 43.86 MJ/kg (ASTM D3338), less than 1 mg/kg sulfur (ASTM D5453), density of 0.7247 (ASTM D4052), and a final boiling point of 232.3° C. (ASTM D86), indicating the majority of this material would be suitable as a blend stock in a fuel application such as diesel or jet fuel.

Example 13

An oligomerization reaction of 1-olefin/1,4-diene (92 wt % 1-decene, 4.5 wt % 1,4-decadiene, 2 wt % 1,4-undecadiene) that was produced from the cross metathesis of palm oil with 1-octene was performed on a 550 g scale using 1.1 mol % ethyl aluminum dichloride (1M solution in hexane)/1.1 mol % tert-butyl chloride for 3 hours at 10° C. The reaction mixture was quenched with water and 1M sodium hydroxide solution and stirred until it became colorless. Hexane (300 ml) was added and mixture was transferred to a separatory funnel. The organic layer was washed with water and brine, and then concentrated on a rotary evaporator to remove the hexane. The oligomeric mixture was devolatilized via short path vacuum distillation (100° C. and 5 Torr) and the product distribution was determined to be 97% mixture oligomers by GC/MS. The dynamic viscosity (Brookfield, #34 spindle, 100 rpm, 22° C.) of the sample is 540 cps. The kinematic viscosity for the sample at 40° C. is 232 cSt.

Example 14

An Aspen model was developed to simulate the process of maximizing the purity of an alpha olefin (i.e., 1-decene) based on the metathesis process of using a soybean oil feed and 1-butene feed at molar ratio of 3:1. A $C_{10}$-$C_{18+}$ olefin stream (Stream A) was created and separated downstream from the cross-metathesis reaction of the soybean oil feed and 1-butene feed. The $C_{10}$-$C_{18+}$ olefin stream was then cross-metathesized with ethylene in a fixed bed ethylene metathesis reactor to create an olefin product. The ethylene product was separated from the olefin product and recycled back to the ethylene metathesis reactor. A heavier olefin product stream (i.e., C16-C18+) was also separated from the olefin product to form a final olefin product (Stream B) and the heavier olefin product stream was recycled back to the ethylene metathesis reactor. The $C_{10}$-$C_{18+}$ olefin input stream (Stream A) and final olefin product stream (Stream B) have the following olefin product distributions, shown in Table 2 below:

TABLE 2

| Olefin Distribution | Stream A wt % | Stream B wt % |
|---|---|---|
| C10:1 | 36.1 | 86.8 |
| C10 isomers | 52.7 | 3.0 |

TABLE 2-continued

| Olefin Distribution | Stream A wt % | Stream B wt % |
|---|---|---|
| C11 | 0.0 | 0.0 |
| C12 | 0.0 | 1.8 |
| C13 | 0.0 | 4.1 |
| C14-18 | 11.2 | 4.3 |
| Total | 100.0 | 100 |

Example 15

An Aspen model was developed to simulate the process of maximizing heavier weight olefins (i.e., $C_{18+}$ olefins) based on the metathesis process of using a soybean oil feed and a hexene isomer feed at molar ratio of 3:1. A $C_{11}$-$C_{18+}$ olefin stream (Stream A) was created and separated downstream from the cross-metathesis reaction of the soybean oil feed and hexene isomer feed. The $C_{11}$-$C_{18+}$ olefin stream was then self-metathesized in a fixed bed reactor to create an olefin product. A $C_{11}$-$C_{16}$ olefin stream was separated from the olefin product recycled back to the self-metathesis reactor. The $C_{10}$ olefin can also be separated as a product to form a final olefin product stream (B). The olefin input stream (Stream A) and final product stream (Stream B) have the following olefin product distributions, shown in Table 3 below:

TABLE 3

| Stream A Olefin Distribution | Stream A wt % | Stream B wt % |
|---|---|---|
| <C10 | 0.0 | 2.5 |
| C10 | 0.0 | 21.3 |
| C11 | 24.7 | 0.0 |
| C12 | 36.2 | 0.0 |
| C13 | 16.8 | 0.0 |
| C14 | 4.5 | 0.0 |
| C15 | 12.1 | 0.0 |
| C16 | 2.4 | 0.0 |
| C17 | 0.4 | 4.1 |
| C18 | 2.4 | 46.7 |
| C18+ | 0.5 | 25.4 |
| Total | 100.0 | 100 |

Example 16

An Aspen model was developed to simulate the process of maximizing the purity of $C_{11}$-$C_{15}$ methyl esters based on the metathesis process of using a soybean oil feed and a hexene isomer feed at molar ratio of 3:1. A mixed triglyceride and ester stream is formed from the cross-metathesis reaction of the soybean oil and hexene isomer feeds. The mixed triglyceride and ester stream undergoes glycerolysis after metathesis, followed by olefin separation and transesterification. A $C_{10}$ and lighter olefin stream is separated from the mixed triglyceride and ester stream and recycled back to the metathesis reactor. A $C_{10}$ methyl ester (ME) stream is also recycled to the metathesis reactor. A $C_{16}$ ME stream is purged. A fraction (e.g., 10%) of the $C_{17}$-$C_{20}$ ME stream is purged and the remaining fraction, mixed with the heavier esters, is recycled back to the metathesis reactor. The final ester product stream (comprising primarily $C_{11}$-$C_{15}$ ME) downstream of the olefin separation, transesterification, and ester recycle streams has the following ester distribution, shown in Table 4:

TABLE 4

| FAME Distribution | Ester Product Stream wt % |
|---|---|
| <C10ME | 0.0 |
| C10ME | 0.0 |
| C11ME | 17.3 |
| C12ME | 21.7 |
| C13ME | 17.7 |
| C14ME | 4.6 |
| C15ME | 16.8 |
| C16ME | 15.6 |
| C17ME | 0.1 |
| C18ME | 6.2 |
| C18 + ME | 0.0 |
| Total | 100.0 |

Example 17

9-DAME/9-DDAME on a 10 g Scale

In this example, methyl 9-decenoate (distillation cut from butenolyzed, stripped, trans-esterified palm oil), and methyl 9-dodecenoate (distillation cut from butenolyzed, stripped, trans-esterified palm oil) were prepared and cross-metathesized. Their compositions are shown in Tables 5 and 6 below. PV was undetected (AOCS method AOCS Method Cd 8b-90 Peroxide Value Acetic Acid—Isooctane Method (Revised 2003)).

TABLE 5

9-DAME Feed composition

| Component | Wt % |
|---|---|
| 1,4-tridecadiene | 0.18 |
| Methyl 8-nonenoate | 0.08 |
| Methyl decanoate | 0.16 |
| Methyl 9-decenoate | 98.51 |
| Methyl 8-decenoate | 0.76 |
| Other | 0.29 |
| TOTAL | 100.00 |

TABLE 6

9-DDAME feed composition

| Component | Wt % |
|---|---|
| 6-pentadecene | 0.18 |
| 3,6-pentadecadiene | 0.21 |
| 7-hexadecene | 0.25 |
| Methyl decanoate | 0.01 |
| Methyl 9-decenoate | 0.76 |
| Methyl decanoate | 3.01 |
| Methyl 9-dodecenoate* | 95.46 |
| Other | 0.12 |
| TOTAL | 100.00 |

*contaminated with 11-isomer dodecenoic acid, methyl ester

Clean, dry, 20 CC scintillation vials outfitted with a magnetic stir bar and septum top were charged with 9-DAME or a mixture of 9-DAME/9-DDAME according to the experiment design Table 7 below.

TABLE 7

| Example | 9-DAME | 9-DDAME | C-827 (ppm wt) | Headspace Treatment |
|---|---|---|---|---|
| 17a (comparative) | 10.02 g | 0 g | 80 | Vent only |
| 17b (comparative) | 10.00 g | 0 g | 80 | Nitrogen purge |
| 17c (comparative) | 10.00 g | 0 g | 500 | Vent only |
| 17d (comparative) | 10.00 g | 0 g | 500 | Nitrogen purge |
| 17e | 4.42 g | 5.60 g | 80 | Vent only |
| 17f | 4.41 g | 5.61 g | 80 | Nitrogen purge |

The vials were placed in an eight-cell aluminum block on top of a heater/stirrer. The aluminum block was heated to 60° C. While the aluminum block was heating (~15 min.), the vial headspace was degassed by providing a nitrogen inlet (~65 mL/min) and an exhaust needle. Meanwhile, a metathesis catalyst solution (0.01 mg/μL) was prepared by first placing C-827 (21.10 mg) in a 2 mL volumetric flask, second capping the flask with a rubber septum, third purging with nitrogen, and fourth adding toluene to the 2.00 mL mark. Metathesis catalyst solution was added to each reaction mixture (time=0). According to the experimental design, the nitrogen inlet (65 mL/min) was left in place to sweep by-product olefins away from the reaction or it was removed. In both cases the vent needle was left in place to avoid over-pressuring the scintillation vial. In the latter case, the oxygen free headspace was provided by olefin formed by metathesis. After 2 hours, the composition (normalized wt %, exclusive of light olefins) was determined by GC FID2, Table 8.

TABLE 8

|  | 17a | 17b | 17c | 17d | 17e | 17f |
|---|---|---|---|---|---|---|
| Methyl 8-nonenoate | 1.39 | 1.67 | 3.58 | 3.65 | 0.00 | 0.00 |
| Methyl 9-decenoate | 80.51 | 77.53 | 41.12 | 28.66 | 28.41 | 17.48 |
| Methyl 8-decenoate | 0.00 | 0.00 | 4.41 | 4.86 | 0.00 | 0.00 |
| Methyl undecenoate | 0.00 | 0.00 | 3.87 | 3.41 | 0.00 | 0.00 |
| Methyl 9-dodecenoate | 0.00 | 0.00 | 0.00 | 0.00 | 29.44 | 12.59 |
| Methyl 9-octadecenoate | 0.09 | 0.10 | 0.18 | 0.19 | 0.35 | 0.58 |
| Dimethyl hexadecenedioate | 0.12 | 0.17 | 0.41 | 0.96 | 0.00 | 0.00 |
| Dimethyl heptadecenedioate | 0.45 | 0.65 | 5.14 | 8.63 | 0.62 | 1.04 |
| Dimethyl 9-octadecenedioate | 16.25 | 18.80 | 39.08 | 46.37 | 36.28 | 62.68 |
| Dimethyl nonadecenedioate | 0.00 | 0.00 | 0.50 | 1.09 | 0.00 | 0.00 |
| Dimethyl eicosenedioate | 0.00 | 0.00 | 0.00 | 0.00 | 0.89 | 1.54 |
| Other | 1.20 | 1.08 | 1.73 | 2.19 | 4.00 | 4.11 |
| Total | 100 | 100 | 100 | 100 | 100 | 100 |

Example 18

9-DAME/9-DDAME on a 330 g Scale

A dibasic ester composition was produced by conducting a cross-metathesis reaction between methyl 9-decenoate (9-decenoic acid methyl ester, 9-DAME) and methyl 9-dodecenoate (9-dodecenoic acid methyl ester, 9-DDAME). A 1.0:1.0 mole ratio mixture of 9-DAME and 9-DDAME (332 g) was charged to a 1 L round bottom flask and heated to 60° C. Pressure was adjusted to 100 mg Hg with ChemGlass diaphragm vacuum pump model CG-4812-30/and J-Kem Scientific Digital Vacuum Regulator Model 200 and stirring was initiated with a magnetic stir bar. The feed composition (distillation cut from butenolyzed, stripped, trans-esterified palm oil) is shown below in Table 9.

TABLE 9

| Component | wt % |
|---|---|
| Methyl decanoate | 0.04 |
| Methyl 9-decenoate | 44.81 |
| Methyl 8-decenoate | 0.07 |
| Methyl undecenoate | 0.19 |
| Methyl decanoate | 0.76 |
| Methyl 9-dodecenoate* | 52.87 |
| Methyl 9,12-tridecadienoate | 0.86 |
| Methyl tetradecenoate | 0.20 |
| Methyl 9-pentadecenoate | 0.03 |
| Methyl 9,12-pentadienoate | 0.02 |
| Methyl hexadecanoate | 0.15 |
| Total | 100 |

*contaminated with methyl 11-dodecenoate

After the system stabilized at desired conditions, 80 ppm of C-827 (as toluene solution) was added (t=0 min). At approximately 15-20 min, the reaction started bubbling vigorously and the pressure rose to approximately 500 mm Hg. Pressure re-stabilized at 100 mm Hg after approximately 5-10 more minutes. Samples were taken at 30, 60, 90, 120, 150, 180, 240, and 300 minutes. At 180 min, an additional 40 ppm of C-827 (as toluene solution) was added.

Figure 2:
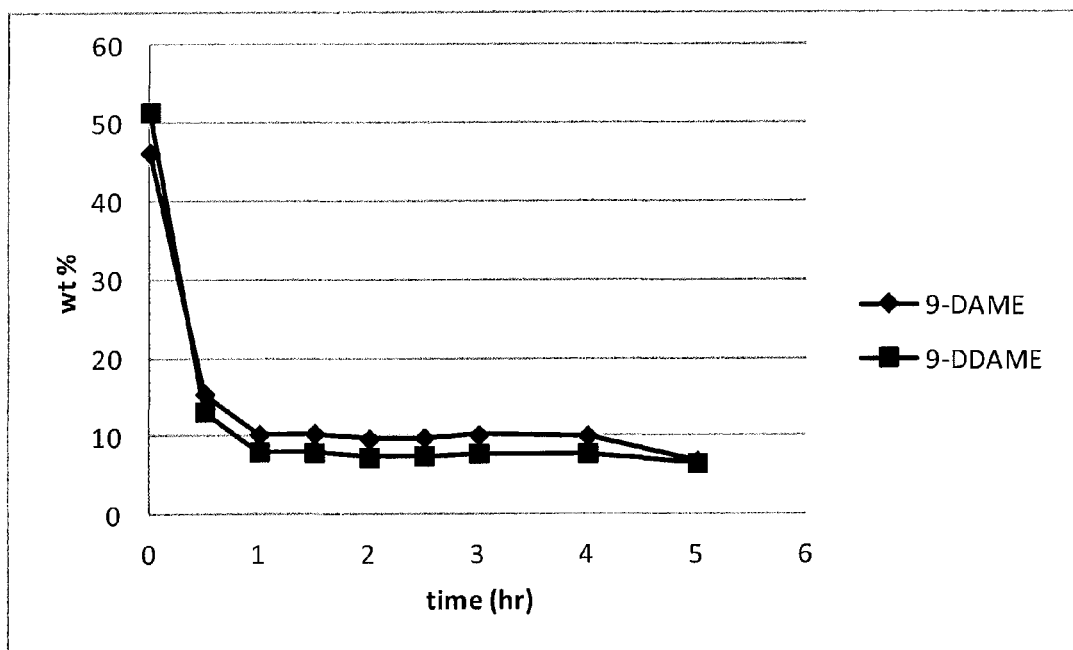
FIG. 2 is a graph of 9-DAME & 9-DDAME (wt %) verses reaction time (hr) for the cross-metathesis reaction between methyl 9-decenoate (9-decenoic acid methyl ester, 9-DAME) and methyl 9-dodecenoate (9-dodecenoic acid methyl ester, 9-DDAME).

The graph in FIG. 2 shows 9-DAME & 9-DDAME (wt %) verses reaction time (hr).

The crude product composition ((normalized wt %, exclusive of light olefins)) at five hours is shown in Table 10 below:

TABLE 10

| FAME | wt % |
|---|---|
| Methyl decanoate | 0.05 |
| Methyl 9-decenoate | 6.79 |
| Methyl 8-decenoate | 0.56 |
| Methyl undecenoate | 0.37 |
| Methyl dodecanoate | 0.84 |
| Methyl 9-dodecenoate* | 6.53 |
| Methyl 9,12-tridecadienoate | 0.05 |
| Methyl tetradecenoate | 0.20 |
| Methyl hexadecanoate | 0.14 |
| Dimethyl hexadecenedioate | 0.07 |
| Dimethyl heptadecenedioate | 1.11 |
| Dimethyl 9-octadecenedioate | 78.92 |
| Dimethyl nonadecenedioate | 0.45 |
| Dimethyl eicosenedioate | 2.85 |
| Dimethyl 9,12-heneicosadienedioate | 0.53 |
| | 99.46 |

*contaminated with methyl 11-dodecenoate

Subsequently, the catalyst was deactivated with 25 equivalents THMP to C-827 at 80° C. for 120 min, THMP being prepared by the general procedure of example 8. The catalyst was then removed by water extraction (5:1 oil to water). The composition was dried with MgSO$_4$. Then, light FAME stripping was conducted at 1 mm Hg and approximately 100° C. The wt % concentration of the various products included a large fraction of 18:1 dibasic ester, see Table 11.

TABLE 11

| Component | Content (wt %) |
|---|---|
| Methyl Hexadecenoate | 0.17 |
| Dimethyl 8-hexadecenedioate | 0.06 |
| Dimethyl 8-heptadecenedioate | 1.34 |
| Dimethyl 9-octadecenedioate | 92.95 |
| Dimethyl nonadecenedioate | 0.58 |
| Dimethyl eicosenedioate | 3.41 |
| Dimethyl 9,12-heneicosadienedioate | 0.92 |
| Heavies | 0.57 |

Example 19

9-DAME/9-DDAME on a 3 kg Scale

A 12 L glass round bottom flask fitted with 1) a reflux condenser (5 C) to which a vacuum gauge and ChemGlass diaphragm vacuum pump model CG-4812-30 where attached, 2) a rubber septum through which nitrogen and catalyst were introduced, magnetic stir bar, and thermocouple and alternate vent (in case vacuum pump failed to maintain sub-atmospheric pressure). No vacuum regulator was used for this example. Heating was provided by heating mantle.

To the nitrogen-purged 12 L reaction-flask was added low PV 9-DAME (1.34 kg) and 9-DDAME (1.68 kg). The condenser was chilled to 5 C with glycol. Under continued flow of nitrogen, the mixture was heated to ~70 C and then placed under full vacuum. The first catalyst solution (C-827 in toluene) addition marked the beginning of the reaction (t=0 min). Temperature and pressure were recorded, see Table 12.

TABLE 12

| Time (min) | Temperature (deg C.) | Pressure (mm Hg) |
|---|---|---|
| 0 | 73.4 | 35.0 |
| 5 | 74.2 | 30.5 |
| 10 | 74.0 | 30.7 |
| 15 | 72.8 | 28.7 |
| 20 | 71.5 | 28.3 |
| 25 | 70.3 | 28.4 |
| 30 | 69.9 | 28.3 |
| 35 | 72.2 | 28.4 |
| 40 | 72.3 | 30.9 |
| 45 | 71.4 | 65.9 |
| 50 | 71.1 | 233.0 |
| 55 | 70.0 | 237.5 |
| 60 | 69.0 | 196.0 |
| 65 | 68.4 | 218.6 |
| 70 | 69.1 | 215.8 |
| 75 | 68.5 | 188.5 |
| 80 | 68.2 | 194.2 |
| 85 | 70.1 | 207.9 |
| 90 | 70.0 | 185.9 |
| 95 | 68.8 | 175.6 |
| 100 | 68.6 | 172.8 |
| 105 | 70.2 | 172.1 |
| 110 | 72.2 | 169.5 |
| 115 | 71.6 | 170.1 |
| 120 | 71.1 | 147.0 |
| 125 | 69.3 | 140.5 |
| 140 | 70.4 | 92.1 |

TABLE 12-continued

| Time (min) | Temperature (deg C.) | Pressure (mm Hg) |
|---|---|---|
| 150 | 69.8 | 74.1 |
| 155 | 71.0 | 68.6 |
| 160 | 71.1 | 64.9 |
| 165 | 70.8 | 57.5 |
| 175 | 69.6 | 57.5 |
| 185 | 70.9 | 56.6 |
| 195 | 67.3 | 54.7 |
| 210 | 63.6 | 56.4 |
| 239 | 56.0 | 64.5 |

Catalyst solution was added in 30 mg increments at 0, 10, 22, 32, 40, 60, 76, 97, 110, 120, and 121 minutes. Total catalyst added was 0.33 g (110 ppm). The reaction initiated about 5 minutes after the fifth increment of catalyst. With each addition of catalyst with exception of the last two, an increased rate of bubbling was observed. After 239 minutes, heat was turned off and the reaction cooled to ambient. Vacuum was turned off and the system was backfilled with nitrogen. A total of 2.66 kg of liquid product were collected. Its composition, analyzed by liquid sample analysis (normalized wt %) is shown in Table 13.

TABLE 13

|  | Initial (wt %) | Final (wt %) |
|---|---|---|
| Butenes | 0.00 | 0.12 |
| 3-hexene | 0.00 | 0.32 |
| 1,4-tridecadiene | 0.03 | 0.00 |
| Pentadecene | 0.09 | 0.00 |
| pentadecadiene | 0.15 | 0.00 |
| Methyl 8-nonenoate | 0.00 | 0.13 |
| Methyl 9-decenoate | 43.59 | 8.65 |
| Methyl 8-decenoate | 0.10 | 0.00 |
| Methyl undecenoate | 0.07 | 0.74 |
| Methyl 9-dodecenoate* | 55.78 | 11.50 |
| Methyl 9,12-tridecadienoate | 0.06 | 0.00 |
| Methyl tetradecenoate | 0.00 | 0.19 |
| Methyl 9-pentadecenoate | 0.00 | 0.19 |
| Methyl 9,12-pentadienoate | 0.00 | 0.08 |
| Methyl 9-octadecenoate | 0.00 | 0.28 |
| Dimethyl hexadecenedioate | 0.00 | 0.16 |
| Dimethyl heptadecenedioate | 0.00 | 2.19 |
| Dimethyl 9-octadecenedioate | 0.13 | 72.41 |
| Dimethyl nonadecenedioate | 0.00 | 0.23 |
| Dimethyl eicosenedioate | 0.00 | 2.74 |
| other | 0.00 | 0.09 |
| TOTAL | 100.00 | 100.00 |

*contaminated with methyl 11-dodecenoate

Samples of the pump exhaust at were collected at 54 minutes (highest off-gas rate) and at 239 minutes (end of experiment) and then analyzed on GASPRO column (see Table 14 below). Formation of ethylene is evidence of 9-DAME self-metathesis. Formation of propylene and 2-butene is evidence of isomerization (for instance 9-DAME to 8-DAME).

TABLE 14

| Gas sample analysis (area %, known components) | | |
|---|---|---|
|  | At 54 minutes | At 239 minutes |
| Ethylene | 1.67 | 0.57 |
| Propylene | 1.07 | 1.84 |
| 1-butene | 92.17 | 46.46 |
| trans-2-butene | 0.08 | 0.09 |
| cis-2-butene | 0.03 | 0.03 |
| trans-3-hexene | 2.95 | 14.99 |
| cis-3-hexene | 1.02 | 2.69 |
| Toluene | 0.62 | 30.15 |

Example 20

9-DAME/9-DDAME on a 10 kg Scale

A clean, dry, stainless steel jacketed 20 liter Parr reactor vessel equipped with a dip tube, overhead stirrer, internal cooling/heated coils, temperature probe, sampling valve, and headspace gas release valve was purged with nitrogen. Pre-mixed 9-DAME/9-DDAME feedstock (10.08 kg, PV=~13) was charged to the reactor; see Table 15 for composition. The reaction was purged with nitrogen through the dip tube at 14.2 L/min (0.5 scfm) for 30 minutes while gently stirring the mixture. The reactor was heated to 200° C. and held for 30 minutes while maintaining a nitrogen purge of 14.2 L/min (0.5 scfm) through the dip tube and a gentle stir rate. The mixture was cooled to 60° C. and nitrogen flow was reduced to 5.7 L/min (0.2 scfm) with continued stirring. The stirrer was turned off and a sample was removed through the sample port. PV was measured and no peroxide detected. GC analysis shown in Table 15. While maintaining gentle stirring and a reactor temperature of 60° C., the reactor pressure was reduced to 100 mm Hg. Catalyst solution (0.33 g of C827 in 40 g of toluene) was added through the sample port (T=0) (9:26). Pressure was maintained at 100 mm Hg with gentle stirring. The first sample (1st metathesis sample) was collected at 1 hr. Another charge of catalyst solution (0.33 g of C827 in 40 g of toluene) was added at 1.5 hr. A second sample (2nd metathesis sample) was collected at 2.25 hr.

TABLE 15

|  | Feed | Heat treated | 1 hr sample | 2.25 hr sample | Final Product |
|---|---|---|---|---|---|
| Methyl 9-decenoate | 43.68 | 42.78 | 10.92 | 8.00 | 6.32 |
| Methyl 9-dodecenoate* | 55.50 | 56.10 | 10.95 | 8.56 | 7.93 |
| Methyl 9,12-tridecadienoate | 0.00 | 0.00 | 0.00 | 0.01 | 0.01 |
| Dimethyl hexadecenedioate | 0.00 | 0.00 | 0.05 | 0.08 | 0.11 |
| Dimethyl heptadecenedioate | 0.00 | 0.00 | 0.54 | 1.17 | 1.79 |
| Dimethyl 9-octadecenedioate | 0.00 | 0.00 | 69.64 | 73.43 | 74.76 |
| Dimethyl nonadecenedioate | 0.00 | 0.00 | 0.11 | 0.25 | 0.38 |
| Dimethyl eicosenedioate | 0.00 | 0.00 | 4.95 | 5.33 | 5.33 |
| Dimethyl 9,12-heneicosadienedioate | 0.00 | 0.00 | 0.34 | 0.24 | 0.25 |
| Other | 0.82 | 1.12 | 2.26 | 2.93 | 3.12 |
| Total | 100.00 | 100.00 | 100.00 | 100.00 | 100.00 |

*contaminated with methyl 11-dodecenoate

The reaction was stopped. A total of 2.9 kg of olefins was collected in cold-traps. Liquid contents of the 20-liter Parr reactor were transferred at 60° C. to a 20-liter nitrogen purged glass reactor and then heated to 80° C. With 567 L/min (20 scfm) of nitrogen flowing through the headspace, a 1 M THMP solution (433 g) was added to the reactor and vigorous stirring was provided. After 2 h, the mixture was cooled to 35° C. and the stirrer was turned off. The reactor was allowed to set overnight. The next day, the mixture was reheated and the temperature was maintained between 50° C. and 55° C. Deionized water (1.8 kg) was added and the two-phase system was vigorously stirred for 30 minutes. The stirrer was turned off to let phases separate. The bottom aqueous phase was removed. Another portion of deionized water (1.8 kg) was added to the reactor. The mixture was stirred well mixed. The stirrer was then turned off to let phases separate. The bottom aqueous phase was removed. The final product (6.29 kg) was removed from the reactor and analyzed by GC.

Example 21

9-DAME/3-Hexene on 10 g Scale

9-DAME composition (distillation cut from butenolyzed, stripped, transesterified palm oil) is given in Table 5. Clean, dry, 20 cc scintillation vials outfitted with a magnetic stir bar and septum top was charged with 9-DAME (PV<1) and 3-hexene (distillation cut of olefins stripped from butenolyzed palm oil) according to the experiment design, Table 16. Each vial was placed in an eight-cell aluminum block on top of a heater/stirrer. The aluminum block was heated to 60° C. While the aluminum block was heating (~15 min), the each vial's headspace was degassed by providing a nitrogen inlet (~65 mL/min) and an exhaust needle. Meanwhile, a 0.01 mg/μL metathesis catalyst solution was prepared by first placing C827 (21.10 mg) in a 2 mL volumetric flask, second capping the flask with a rubber septum, third purging with nitrogen, and fourth adding toluene to the 2.00 mL mark. Metathesis catalyst was added to the reaction mixture (time=0). According to the experimental design, the nitrogen inlet (65 mL/min) was left in place to sweep by-product olefins away from the reaction or it was removed. In both cases the vent needle was left in place. In the latter case, olefin formed by metathesis provided the oxygen-free environment needed by the catalyst. After 2 hours, an aliquot was analyzed by GC. Composition ((normalized wt %, exclusive of light olefins) is shown in Table 17.

TABLE 16

| Example | 9-DAME | 3-Hexene | C-827 (ppm wt) | Headspace treatment |
|---|---|---|---|---|
| 21a | 6.42 g | 3.61 g | 80 | Vent only |
| 21b | 6.43 g | 3.66 g | 80 | Nitrogen purge |
| 21c | 6.42 g | 3.60 g | 120 | Vent only |
| 21d | 6.44 g | 3.58 g | 120 | Nitrogen purge |

TABLE 17

| Example | 21a | 21b | 21c | 21d |
|---|---|---|---|---|
| Methyl 8-nonenoate | 0.00 | 0.00 | 0.00 | 0.00 |
| Methyl 9-decenoate | 72.85 | 0.44 | 10.91 | 0.46 |
| Methyl 8-decenoate | 0.90 | 0.00 | 0.00 | 0.00 |
| Methyl undecenoate | 0.00 | 0.00 | 2.17 | 0.00 |
| Methyl 9-dodecenoate | 23.24 | 19.45 | 58.87 | 19.34 |
| Methyl tridecenoate | 0.00 | 0.00 | 0.00 | 0.00 |
| Methyl tetradecenoate | 0.00 | 0.00 | 0.00 | 0.00 |
| Methyl 9-octadecenoate | 0.00 | 0.00 | 0.14 | 0.40 |
| Dimethyl hexadecenedioate | 0.00 | 0.00 | 0.00 | 0.00 |
| Dimethyl heptadecenedioate | 0.10 | 1.75 | 0.79 | 1.95 |
| Dimethyl 9-octadecenedioate | 1.68 | 74.27 | 24.48 | 73.96 |
| Other | 1.23 | 4.09 | 2.64 | 3.88 |
| Total | 100.00 | 100.00 | 100.00 | 100.00 |

Example 22

9-DAME/trans-2-butene on 40 g Scale

9-DAME (40.16 g) was charged to a 100 mL 3-neck round bottom flask fitted with a coil-type reflux condenser (exhausted to an oil bubbler), a magnetic stir bar, and septum caps. The reaction system was purged, for 30 minutes, with nitrogen by a needle inserted into one of the septum caps and allowing the exhaust out the bubbler. The reaction flask was immersed in an oil batch which was heated to 55° C. The condenser was cooled by means of 15° C. glycol fluid. Nitrogen purge was replaced by a flow of trans-2-butene through the liquid. After a consistent reflux of trans-2-butene was observed, 80 ppm catalyst was added (T=0). The flow of trans-2-butene was continued for the duration of the reaction except as follows. The reaction was monitored by interrupting trans-2-butene flow and observing bubble rate in the bubbler. In addition to the initial 80 ppm charge of catalyst, three additional 20 ppm increments of catalyst were added at T=30, 81, 125 minutes. Final product weight was 31.25 g. Conversion to diesters was 85% and selectivity to 9-ODDAME was 81%.

Example 23

9-DAME/trans-2-butene in Fisher-Porter Tube

Using a 3 ounce Fisher-Porter tube equipped with an addition ports for catalyst and trans-2-butene. In a glove box, 40.0 mg C827 was dissolved in 1 mL of toluene. Sixty microliters of catalyst solution were loaded into the catalyst addition manifold using a 250 uL syringe, removed from glove box, and attached to the pressure vessel manifold. Twenty grams of 9-DAME charged to the pressure tube which was subsequently degassed for 30 minutes with nitrogen. Meanwhile trans-2-butene was condensed/transferred into a second 3-ounce Fisher-Porter tube. The pressure vessel containing trans-2-butene was pressured with nitrogen to 4 psig. The pressure vessel containing the ester was heated to 60° C. in a silicone oil bath. The catalyst solution was transferred to the ester under nitrogen. Immediately, about 7.6 mL (4.57 g) of trans-2-butene (target for 0.75:1 ratio) was transferred to the pressure vessel containing the 9-DAME, which washed any residual catalyst solution into the reaction vessel.

The volume was measured using mm graduation marks on the vessel and the measured cross sectional area of the tube. The targeted volume was based on converting the targeted mass to a targeted volume assuming a trans-2-butene density of 0.6 g/mL. The pressure tube containing the reaction mixture was then pressurized to 36 psig with nitrogen. Samples were taken at 10 minutes and 60 minutes using a sampling tube apparatus. The vessel was depressurized slowly to atmospheric pressure and sparged with nitrogen. After 60 minutes of sparging, the vessel was disassembled, and the sample was collected. The pressure, bath temperature, and liquid level were monitored as a function of time and summarized in Table 18. GC analysis (normalized wt %, exclusive of light olefins) is summarized in Table 19.

TABLE 18

| Time (min) | Pressure (psig) | Temperature (° C.) | Liquid level (mm) | Comments |
|---|---|---|---|---|
| 0 | 36 | 58.9 | 60.5 | Closed system |
| 5 | 76 | 59.2 | 55.0 | Closed system |

TABLE 18-continued

| Time (min) | Pressure (psig) | Temperature (° C.) | Liquid level (mm) | Comments |
|---|---|---|---|---|
| 10 | 83 | 59.3 | 55.0 | Closed system, Sample #1 |
| 10 | 84 | 59.2 | 53.5 | Closed system |
| 15 | 84 | 59.1 | 53.5 | Closed system |
| 20 | 88 | 59.1 | 54.0 | Closed system |
| 30 | 91 | 58.9 | 53.5 | Closed system |
| 40 | 92 | 58.9 | 53.5 | Closed system |
| 50 | 92 | 58.9 | 53.5 | Closed system |
| 60 | 92 | 58.9 | 53.5 | Closed system, Sample #2 |
| 60 | 96 | 58.9 | 43.5 | Nitrogen sparge |
| 120 | 0 | | | Reaction End, Sample #3 |

TABLE 19

| | Sample 1 (10 min) | Sample 2 (60 min) | Sample 3 (120 min) |
|---|---|---|---|
| Methyl 9-decenoate | 36.2 | 36.9 | 35.3 |
| Methyl undecenoate | 31.9 | 39.0 | 39.1 |
| Methyl 8-decenoate | 2.5 | 4.3 | 5.6 |
| Methyl 8-nonenoate | 1.3 | 1.4 | 1.3 |
| Dimethyl hexadecenedioate | 0.2 | 0.1 | 0.2 |
| Dimethyl heptadecenedioate | 2.4 | 1.8 | 1.9 |
| Dimethyl 9-octadecenedioate | 25.4 | 16.4 | 16.6 |
| Dimethyl nonadecenedioate | 0.1 | 0.1 | 0.1 |

Example 24

9-DAME/trans-2-butene on 8 kg Scale

A two-stage cross-metathesis strategy using 9-DAME and purchased trans-2-butene was employed. In the first stage, 9-DAME was partially converted in situ to 9-UDAME. In the second stage, the mixture of 9-DAME and 9-UDAME was converted to 9-ODDAME. The 9-DAME feedstock (from octenolyzed palm oil) for this example was contaminated with significant concentrations of 8-DAME and 7-tetradecene, Table 20.

TABLE 20

| | Lot A (wt %) | Lot B (wt %) |
|---|---|---|
| Methyl 9-decanoate | 81.4 | 88.6 |
| Methyl 8-decanoate | 8.9 | 5.7 |
| 7-tetradecene | 8.0 | 4.6 |

The two-stage synthesis was performed eight times and was found to scale-up without difficulties. The first batch was performed using an initial 4 kg charge of an 81% pure 9-DAME and 1.2 mol trans-2-butene/mol 9-DAME, yielding a crude product containing 57 wt % 9-ODDAME. The second preparation used a 6 kg charge of the 81% pure 9-DAME and only 0.75 mol trans-2-butene/mol 9-DAME, yielding a crude product containing 53 wt % 9-ODDAME. The remaining preparations used 8 kg initial charges of 89% pure 9-DAME and 0.75 mol trans-2-butene/mol 9-DAME, yielding crude products containing from 60 to 69 wt % 9-ODDAME. Table 21 summarizes key reaction measures for the eight batches. Composition is in normalized wt %, exclusive of light olefins.

TABLE 21

| | Run # | | | | | | | |
|---|---|---|---|---|---|---|---|---|
| | 24a | 24b | 24c | 24d | 24e | 24f | 24g | 24h |
| 9-DAME lot | A | A | B | B | B | B | B | B |
| Run size | | | | | | | | |
| (kg 9-DAME) | 4 | 6 | 8 | 8 | 8 | 8 | 8 | 8 |
| (kg trans-2-butene) | 1.4 | 1.4 | 1.9 | 1.9 | 1.9 | 1.9 | 1.9 | 1.9 |
| Molar ratio (2-butene:9-DAME) | 1.2 | 0.75 | 0.75 | 0.75 | 0.75 | 0.75 | 0.75 | 0.75 |
| C-827 charge (ppmwt) | | | | | | | | |
| stage 1 | 93 | 68 | 68 | 68 | 68 | 68 | 68 | 68 |
| stage 2 | 93 | 68 | 68 | 68 | 68 | 68 | 68 | 68 |
| Stage 1 wt ratio 9-UDAME:9-DAME | 4.93 | 2.43 | 2.21 | 2.37 | 1.88 | 1.92 | 1.98 | NA |
| Stage 2 composition (wt %) | | | | | | | | |
| 1-octene | 0.00 | 0.00 | 0.31 | 0.18 | 0.31 | 0.00 | 0.00 | 0.00 |
| 2-nonene | 0.00 | 2.62 | 1.09 | 0.48 | 0.68 | 1.17 | 0.58 | 0.46 |
| 7-tetradecene | 0.75 | 0.75 | 0.20 | 0.18 | 0.25 | 0.27 | 0.11 | 0.22 |
| Methyl decanoate | 0.35 | 0.43 | 0.42 | 0.41 | 0.55 | 0.65 | 0.69 | 0.00 |
| Methyl 9-decenoate | 0.23 | 1.02 | 2.08 | 1.90 | 2.84 | 2.20 | 1.69 | 1.70 |
| Methyl 8-decenoate | 0.38 | 1.71 | 0.86 | 0.65 | 0.91 | 1.14 | 0.89 | 1.04 |
| Methyl undecenoate | 2.13 | 13.64 | 10.38 | 8.47 | 11.57 | 14.00 | 11.66 | 11.43 |
| Methyl pentadecenoate | 1.39 | 0.08 | 0.50 | 0.58 | 0.68 | 0.77 | 0.65 | 0.66 |
| Methyl hexadecenoate | 10.30 | 9.64 | 5.14 | 5.83 | 6.46 | 6.96 | 6.46 | 6.68 |
| Methyl heptadecenoate | 2.08 | 0.28 | 0.00 | 0.00 | 0.19 | 0.22 | 0.19 | 0.20 |
| Dimethyl hexadecenedioate | 1.19 | 1.18 | 0.96 | 1.11 | 1.11 | 1.15 | 1.12 | 1.08 |
| Dimethyl heptadecenedioate | 13.02 | 12.24 | 9.26 | 9.91 | 9.54 | 9.42 | 9.64 | 9.40 |
| Dimethyl 9-octadecenedioate | 57.05 | 53.15 | 66.79 | 68.68 | 64.20 | 60.34 | 65.06 | 65.24 |
| Total | 97.06 | 96.74 | 97.99 | 98.39 | 99.28 | 98.29 | 98.74 | 98.10 |

Purification was accomplished in approximately 2 kg batches by crystallizing trans-ODDAME from crude product using four volumes of cold methanol, vacuum filtration including a wash with additional cold methanol, and then vacuum drying. Typical yield was about 50% and typical purity is shown in Table 22.

TABLE 22

|  | From lot A feed | From lot B feed |
|---|---|---|
| Dimethyl 9-octadecenedioate | 96.9 | 97.6 |

Example 30

Time of trishydroxymethyl phosphine (THMP) treatment and water treatment, as well as type of water, were varied to study the effects on ruthenium removal from a natural oil/metathesis catalyst solution.

In the experiments described, THMP was supplied from a stock solution by the following method: 10.20 g of 75 wt % tetrakishydroxymethyl phosphonium sulfate in water (Bricorr 75, Rhodia) was diluted with 37.69 deionized water (Type II) under an nitrogen-inserted atmosphere 4.02 g of 50 wt % sodium hydroxide (Aldrich) was then added to the diluted solution, followed by the addition of 4.08 g of 75 wt % tetrakishydroxymethyl phosphonium sulfate to the mixture, to adjust the pH to 8. The pH of the solution was measured using a pH probe. The solution was transferred to a plastic container and stored until use. The molar concentration of THMP in the solution was based on the total amount of the limiting reagent sodium hydroxide (1 mole of trishydroxymethyl phosphine=1 mole of sodium hydroxide in excess tetraki. In a 500 mL kettle flask (4 inch inner diameter), equipped with an overhead stirrer (4-pitch blades, 45°, 2 inch diameter), overhead condenser (set at 5° C.), and baffles, a water stream containing extracted ruthenium and trishydroxymethyl phosphine (derived from tetrakis hydroxymethyl phosphonium sulfate) was generated by the following procedure:shydroxymethyl phosphonium sulfate).

In a 500 mL kettle flask (4 inch inner diameter), equipped with an overhead stirrer (4-pitch blades, 45°, 2 inch diameter), overhead condenser (set at 5° C.), and baffles, a water stream containing extracted ruthenium and trishydroxymethyl phosphine (derived from tetrakis hydroxymethyl phosphonium sulfate) was generated by the following procedure: 1-octene (Aldrich, 98%) was reacted with palm oil (Wilmar, refined, bleached, deodorized, pretreated at 200° C. for 2 hours batch under nitrogen sparging) at a 1.5:1 molar double bond ratio of 1-octene: palm oil in the presence of 800 ppmw catalyst (C827, Materia, based on mass of oil), 60 minute batch contact time, 60° C. reaction temperature, atmospheric pressure, and under a nitrogen-blanketed headspace. After generating the metathesized mixture, the mixture was heated to 90° C. and 19:1 molar equivalents of trishydroxymethyl phosphine to catalyst (target) was added to the metathesized mixture. The metathesized mixture containing trishydroxymethyl phosphine was stirred for 60 minutes batch. Then, deionized water (Type II) was added to the metathesized mixture at 1 g of water to 5 g of metathesized oil and stirred for 1 hour, batch at 72 to 90° C. After 1 hour of water mixing, the mixture was allowed to gravity settle for 1 hour while heating at 90° C. The bottom layer was removed from the mixture and stored. This bottom layer was assumed to simulate a 20:1 recycle ratio of water in a continuous extraction process (based on a typical 40 ppmw catalyst concentration, based on mass of oil), and referred to as "Simulated Recycled Water Stream" herein.

Additional metathesized mixtures of oil were generated by reacting 1-octene with palm oil (1.5:1 molar double bond ratio of 1-octene: palm oil) in the presence of 40 ppmw catalyst (based on mass of oil), 60 minute batch contact time, 60° C. reaction temperature, atmospheric pressure, and under a nitrogen-blanketed headspace. A sample was removed after 60 minutes to analyze for ruthenium concentration. Samples generated from the method described are referred to as "Before THMP Treatment" herein.

After generating the additional metathesized mixture, the mixture was heated to 90° C., and 19:1 molar equivalents of trishydroxymethyl phosphine to catalyst (target) was added to the metathesized mixture. The metathesized mixture containing trishydroxymethyl phosphine was stirred for 60 minutes batch. Samples generated from the method described are referred to as "After THMP Treatment" herein.

Then, the simulated recycled water was added to the metathesized mixture at 1 g of water to 5 g of metathesized oil and stirred for various times (15 minutes, 30 minutes, 60 minutes) batch at 72 to 90° C. After water mixing, the mixture was allowed to gravity settle for 1 hour at 90° C. The top layer and bottom layers were sampled for ruthenium concentration and the top layer was sampled for isomerization testing. Samples generated from the method described are referred to as "After Water Extraction" herein.

Ruthenium analysis was performed using ICP-MS at STAT Analysis Corporation, Chicago, Ill. Ruthenium efficiency (%), assuming mass is conserved, is defined by the following equation:

$$\text{Ruthenium Removal Efficiency (\%)} = 100 \frac{C_{Ru\,Before\,Extraction} - C_{Ru\,After\,Extraction}}{C_{Ru\,Before\,Extraction}} \#$$

Isomerization tests were performed on the samples to determine the effectiveness of the trishydroxymethyl phosphine reaction with the ruthenium-containing catalyst. The isomerization test included heating the sample to 250° C. for 1 hour under an open-system nitrogen headspace, maintained at 1 psig.

Standard sample analysis was performed on the isomerized samples. About 6 drops (~100-200 mg) of the sample were transferred to a 20 mL borosilicate scintillation vial. 1 mL of 1 mass % sodium methoxide in methanol (Aldrich) was added to the vial using an autopipette. The vial was sealed and was heated to 60 C while shaken at 240 rpm for at least 40 minutes until one liquid phase was visually observed. 5 mL of saturated brine solution was added to the vial using an autopipette. 5 mL of ethyl acetate was then added to the vial using an autopipette. The mixture was further shaken and allowed to settle into two distinct phases. Approximately 1.5-2 mL of the top layer (ethyl acetate) was transferred to a 2 mL gas chromatography vial.

The vial was analyzed for 9-decenoic acid ester isomerization using an Agilent 7890 gas chromatograph, equipped with a split/splitlless injection port, an RTX-65TG column (Restek 17008, 30 m length×0.25 mm inner diameter×0.1 mm film thickness), quadrupole mass spectrometer detector. Helium was used as the carrier gas.

The 9-decenoic acid ester and isomers were quantified using ion extraction of the ester fragments with the MS Chem software; the integrated areas were assumed to be proportional to the relative mass concentration of the esters.

The percent isomerization was defined by the following equation:

$$\text{Isomerization (\%)} = 100 \frac{A_{Isomer1} + A_{Isomer2} + A_{Isomer3}}{A_{Isomer1} + A_{Isomer2} + A_{Isomer3} + A_{9\text{-}Decenoic\ Acid\ Ester}} \#$$

where $A_{Isomer\ 1}$ is the integrated area of isomer 1 of 9-decenoic acid ester, $A_{Isomer\ 2}$ is the integrated area of isomer 2 of 9-decenoic acid ester, $A_{Isomer\ 3}$ is the integrated area of isomer 3 of 9-decenoic acid ester, $A_{9\text{-}Decenoic\ Acid\ Ester}$ is the integrated area of 9-decenoic acid ester. Isomer 1 and 2 are the cis- and trans-8-decenoic acid methyl esters. Isomer 3 is a 7-decenoic acid methyl ester. Other isomers can form, but are not chromatographically resolved from the peaks observed.

Testing was performed within 24 hours of sampling from reactor vessel. For most cases, the testing was within an hour of sampling. Sample analysis was run in duplicate, and an average of two runs is reported. For reference, the result of the isomerization test on a sample not treated with THMP was typically 20-40% isomerization (average of two samples) at the catalyst loadings studied.

Split ratio: ~50:1

The products were characterized by comparing peaks with known standards, in conjunction with supporting data from mass spectrum analysis (GCMS-Agilent 5973N). GCMS analysis was accomplished with a second Rtx-5, 30 m×0.25 mm (ID)×0.25 µm film thickness GC column, using the same method as above.

Alkane analyses were performed using an Agilent 6850 instrument and the following conditions:
  Column: Restek Rtx-65, 30 m×0.32 mm (ID)×0.1 µm film thickness
  Injector temperature: 250° C.
  Detector temperature: 350° C.
  Oven temperature: 55° C. starting temperature, 5 minute hold time, ramp rate 20° C./min to 350° C., 10 minute hold time
  Carrier gas: Hydrogen
  Flow rate: 1.0 mL/min
  Split ratio: 40:1

The products were characterized by comparing peaks with known standards. Fatty acid methyl ester (FAME) analyses were performed using an Agilent 6850 instrument and the following conditions:
  Column: J&W Scientific, DB-Wax, 30 m×0.32 mm (ID)× 0.5 µm film thickness
  Injector temperature: 250° C.

| Water Type | Process | Conditions | Isom % | Water content (ppmw) | Ru (ppmw) | Ru removal eff (%) |
|---|---|---|---|---|---|---|
| Type II DI | 60 min THMP treatment, 60 min water extraction, and 60 min settling | Before THMP treatment | 44.41 | 93 | 3.8 | 80 |
| | | After THMP treatment | 0.08 | 88 | — | |
| | | After water extraction | 0.18 | 1524 | 0.75 | |
| Simulated recycled, 20 recycles, ~360 ppmw Ru | 60 min THMP treatment, 60 min water extraction and 60 min settling | Before THMP treatment | 31.10 | 51 | 3.4 | 47 |
| | | After THMP treatment | 0.60 | 51 | — | |
| | | After water extraction | 0.69 | 1162 | 1.8 | |
| Simulated recycled, 20 recycles, ~360 ppmw Ru | 60 min THMP treatment, 30 min Water Extraction, and 60 min settling | Before THMP treatment | 34.70 | 50 | 5 | 48 |
| | | After THMP treatment | 0.06 | 57 | — | |
| | | After water extraction | 0.28 | 1657 | 2.6 | |
| Simulated recycled, 20 recycles, ~360 ppmw Ru | 60 min THMP treatment, 15 min water extraction, and 60 min settling | Before THMP treatment | 43.25 | 28 | 9.3 | 63 |
| | | After THMP treatment | 1.06 | 37 | — | |
| | | After water extraction | 0.21 | 1733 | 3.4 | |
| Simulated recycled, 20 recycles, ~360 ppmw Ru | 0 min THMP treatment, 60 min water extraction, and 60 min settling | Before THMP treatment | 31.65 | 43 | 6.2 | 42 |
| | | — | — | — | — | |
| | | After water extraction | 0.57 | 1750 | 3.6 | |
| Simulated recycled, 20 recycles, ~320 ppmw Ru | 15 min THMP treatment, 15 min water extraction, and 60 min settling | Before THMP treatment | 33.5 | 125.1 | 3.5 | 46 |
| | | After THMP treatment | 0.50 | 1854 | — | |
| | | After water extraction | 0.31 | 974 | 1.9 | |

Unless otherwise described, the aforementioned examples utilized the following analytical methods described below:

Volatile products were analyzed by gas chromatography and flame ionization detector (FID). Alkene analyses were performed using an Agilent 6890 instrument and the following conditions:
  Column: Restek Rtx-5, 30 m×0.25 mm (ID)×0.25 µm film thickness
  Injector temperature: 250° C.
  Detector temperature: 280° C.
  Oven temperature: 35° C. starting temperature, 4 minute hold time, ramp rate 12° C./min to 260° C., 8 minute hold time
  Carrier gas: Helium
  Mean gas velocity: 31.3±3.5% cm/sec (calculated)

Detector temperature: 300° C.
  Oven temperature: 70° C. starting temperature, 1 minute hold time, ramp rate 20° C./min to 180° C., ramp rate 3° C./min to 220° C., 10 minute hold time
  Carrier gas: Hydrogen
  Flow rate: 1.0 mL/min The examples above collectively demonstrate the major steps described in the process schemes, showing the production of olefins, paraffins, metathesized triglycerides, unsaturated fatty acid esters and acids, and diacid compounds from natural oils that are useful as chemicals, solvents and fuels blending stocks.

What is claimed is:

1. A method of refining a natural oil, comprising:
  providing a feedstock comprising a natural oil;

reacting the feedstock in a metathesis reactor in the presence of a first metathesis catalyst to form a metathesized product comprising olefins and esters;

separating the olefins in the metathesized product from the esters in the metathesized product;

transesterifying the esters in the presence of an alcohol to form a transesterified product comprising a terminal olefin ester having the following structure:

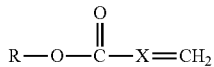

wherein X is a $C_3$-$C_{18}$ saturated or unsaturated alkyl chain, and R is an alkyl group;

and reacting the terminal olefin ester with an internal olefin ester in the presence of a second metathesis catalyst to form a dibasic ester.

2. The method of claim 1, wherein R is methyl.

3. The method of claim 1, wherein the weight ratio of the terminal olefin ester to the internal olefin ester is between 5:1 and 1:5.

4. The method of claim 1, wherein the weight ratio of the terminal olefin ester to the internal olefin ester is 1:1.

5. The method of claim 1, wherein the terminal olefin ester is selected from the group consisting of: 4-pentenoic acid ester, 5-hexenoic acid ester, 6-heptenoic acid ester, 7-octenoic acid ester, 8-nonenoic acid ester, 9-decenoic acid ester, 10-undecenoic acid ester, 11-dodecenoic acid ester, 12-tridecenoic acid ester, 13-tetradecenoic acid ester, 14-pentadecenoic acid ester, 15-hexadecenoic acid ester, 16-heptadecenoic acid ester, 17-octadecenoic acid ester, and mixtures thereof.

6. The method of claim 1, wherein the terminal olefin ester is 9-decenoic acid ester.

7. The method of claim 1, wherein the internal olefin ester is selected from the group consisting of: pentenoic acid esters, hexenoic acid esters, heptenoic acid esters, octenoic acid esters, nonenoic acid esters, decenoic acid esters, undecenoic acid esters, dodecenoic acid esters, tridecenoic acid esters, tetradecenoic acid esters, pentadecenoic acid esters, hexadecenoic acid esters, heptadecenoic acid esters, octadecenoic acid esters, and mixtures thereof.

8. The method of claim 1, wherein the internal olefin ester is 9-dodecenoic acid ester.

9. The method of claim 1, further comprising providing a low-molecular-weight olefin or a mid-weight olefin, wherein the reacting step comprises a cross-metathesis reaction between the feedstock and the low-molecular-weight olefin or mid-weight olefin.

10. The method of claim 9, wherein the low-molecular-weight olefin comprises at least one low-molecular-weight olefin selected from the group consisting of propylene, 1-butene, 2-butene, 3-hexene, and mixtures thereof.

11. The method of claim 1, wherein the internal olefin ester is formed by reacting a portion of the terminal olefin ester with a low-molecular-weight internal olefin in the presence of a third metathesis catalyst.

12. The method of claim 11, wherein the low-molecular-weight internal olefin is selected from the group consisting of: 2-butene, 2-pentene, 2-hexene, 3-hexene, 2-heptene, 3-heptene, 2-octene, 3-octene, 2-nonene, 3-nonene, and mixtures thereof.

13. The method of claim 11, wherein the low-molecular-weight internal olefin is 3-hexene.

14. The method of claim 1, wherein the dibasic ester is 9-octadecene dioic acid dimethyl ester.

15. The method of claim 1, further comprising hydrolyzing the dibasic ester.

16. The method of claim 1, wherein the olefin byproduct is removed from the metathesis product during the reaction of the terminal olefin and internal olefin, improving the yield of the dibasic ester and/or dibasic acid.

17. The method of claim 1, wherein at least 70 wt % dibasic ester and/or dibasic acid is formed in the presence of less than 150 ppm.

18. A method of refining a natural oil, comprising:

providing a feedstock comprising a natural oil;

reacting the feedstock in a metathesis reactor in the presence of a first metathesis catalyst to form a metathesized product comprising olefins and esters;

separating the olefins in the metathesized product from the esters in the metathesized product;

transesterifying the esters in the presence of an alcohol to form a transesterified product comprising 9-decenoic acid ester; and reacting the 9-decenoic acid ester with 9-dodecenoic acid ester in the presence of a second metathesis catalyst to form 9-octadecene dioic acid ester.

19. The method of claim 18, wherein the 9-dodecenoic acid ester is formed by reacting a portion of the 9-decenoic acid ester with a low-molecular-weight internal olefin or a mid-weight internal olefin in the presence of a third metathesis catalyst.

20. The method of claim 19, wherein the low-molecular-weight internal olefin is 3-hexene.

21. The method of claim 18, further comprising hydrolyzing the 9-octadecene dioic acid ester to form 9-octadecene dioic acid.

* * * * *